United States Patent
Sharkey et al.

(10) Patent No.: US 10,070,958 B2
(45) Date of Patent: *Sep. 11, 2018

(54) SUBCHONDRAL TREATMENT TO PREVENT THE PROGRESSION OF OSTEOARTHRITIS OF THE JOINT

(71) Applicant: ZIMMER KNEE CREATIONS, INC., Exton, PA (US)

(72) Inventors: Peter F. Sharkey, Villanova, PA (US); Charles F. Leinberry, Chester Springs, PA (US)

(73) Assignee: ZIMMER KNEE CREATIONS, INC., Exton, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/824,826

(22) Filed: Nov. 28, 2017

(65) Prior Publication Data

US 2018/0078376 A1    Mar. 22, 2018

Related U.S. Application Data

(63) Continuation of application No. 15/616,587, filed on Jun. 7, 2017, now Pat. No. 9,913,721, which is a (Continued)

(51) Int. Cl.
*A61F 2/28* (2006.01)
*A61F 2/30* (2006.01)
(Continued)

(52) U.S. Cl.
CPC ........ *A61F 2/30756* (2013.01); *A61F 2/4601* (2013.01); *A61F 2/4603* (2013.01); *A61F 2/4657* (2013.01); *A61B 17/1764* (2013.01); *A61B 17/3423* (2013.01); *A61B 17/3472* (2013.01); *A61F 2002/2817* (2013.01); *A61F 2002/2835* (2013.01);
(Continued)

(58) Field of Classification Search
CPC .............. A61F 2/389; A61F 2002/2835; A61F 2002/2892
See application file for complete search history.

(56) References Cited

U.S. PATENT DOCUMENTS

| 5,514,137 A | 5/1996 | Coutts |
| 5,556,429 A | 9/1996 | Felt |

(Continued)

OTHER PUBLICATIONS

"U.S. Appl. No. 13/568,522, Advisory Action dated Mar. 18, 2015", 2 pgs.
(Continued)

*Primary Examiner* — David H Willse
*Assistant Examiner* — Javier Blanco
(74) *Attorney, Agent, or Firm* — Schwegman Lundberg & Woessner, P.A.

(57) ABSTRACT

Methods for the prevention, or delayed onset or progression of, bone marrow edema or bone marrow lesion, and subchondral treatment to prevail the progression of osteoarthritis of a joint are disclosed. The methods involve treating the subchondral bone, while preserving, as much as possible, the joint's articular and cartilage surface. The methods could be performed before, during, or after an initial arthroscopic surgery to repair the joint. Associated devices and instruments for treatment of the subchondral bone are also disclosed.

16 Claims, 22 Drawing Sheets

Related U.S. Application Data continuation of application No. 15/359,842, filed on Nov. 23, 2016, now Pat. No. 9,707,081, which is a continuation of application No. 14/733,334, filed on Jun. 8, 2015, now Pat. No. 9,532,876, which is a continuation of application No. 13/568,522, filed on Aug. 7, 2012, now Pat. No. 9,119,646.

(60) Provisional application No. 61/515,953, filed on Aug. 7, 2011.

(51) Int. Cl.
| | |
|---|---|
| A61F 2/38 | (2006.01) |
| A61F 2/46 | (2006.01) |
| A61B 17/34 | (2006.01) |
| A61B 17/17 | (2006.01) |

(52) U.S. Cl.
CPC .......... *A61F 2002/2839* (2013.01); *A61F 2002/2892* (2013.01); *A61F 2002/30011* (2013.01); *A61F 2002/30014* (2013.01); *A61F 2002/4635* (2013.01); *A61F 2002/4662* (2013.01)

(56) References Cited

U.S. PATENT DOCUMENTS

| | | | |
|---|---|---|---|
| 5,755,809 | A | 5/1998 | Cohen et al. |
| 6,140,452 | A | 10/2000 | Felt et al. |
| 6,235,043 | B1 | 5/2001 | Reiley et al. |
| 6,241,734 | B1 | 6/2001 | Scribner et al. |
| 6,248,110 | B1 | 6/2001 | Reiley et al. |
| 6,306,177 | B1 | 10/2001 | Felt et al. |
| 6,395,007 | B1 | 5/2002 | Bhatnagar et al. |
| 6,564,083 | B2 | 5/2003 | Stevens |
| 6,607,561 | B2 | 8/2003 | Brannon |
| 6,613,054 | B2 | 9/2003 | Scribner et al. |
| 6,719,761 | B1 | 4/2004 | Reiley et al. |
| 6,746,451 | B2 | 6/2004 | Middleton et al. |
| 6,827,720 | B2 | 12/2004 | Leali |
| 6,863,899 | B2 | 3/2005 | Koblish et al. |
| 6,887,246 | B2 | 5/2005 | Bhatnagar et al. |
| 7,153,307 | B2 | 12/2006 | Scribner |
| 7,217,294 | B2 | 5/2007 | Kusanagi et al. |
| 7,261,720 | B2 | 8/2007 | Stevens et al. |
| 7,708,742 | B2 | 5/2010 | Scribner et al. |
| 7,771,431 | B2 | 8/2010 | Scribner et al. |
| 7,811,290 | B2 | 10/2010 | Rabiner |
| 7,867,235 | B2 | 1/2011 | Fell et al. |
| 8,062,364 | B1 | 11/2011 | Sharkey et al. |
| 8,152,813 | B2 | 4/2012 | Osorio et al. |
| 8,168,692 | B2 | 5/2012 | Wenz |
| 9,119,646 | B2 | 9/2015 | Sharkey et al. |
| 9,532,876 | B2 | 1/2017 | Sharkey et al. |
| 9,707,081 | B2 | 7/2017 | Sharkey et al. |
| 2003/0138473 | A1 | 7/2003 | Koblish et al. |
| 2003/0216669 | A1 | 11/2003 | Lang et al. |
| 2004/0028717 | A1 | 2/2004 | Sittinger et al. |
| 2004/0242987 | A1 | 12/2004 | Liew et al. |
| 2005/0119219 | A1 | 6/2005 | Bellini et al. |
| 2006/0064164 | A1 | 3/2006 | Thelen et al. |
| 2010/0076503 | A1 | 3/2010 | Beyar et al. |
| 2010/0145451 | A1 | 6/2010 | Dee |
| 2010/0179549 | A1 | 7/2010 | Keller et al. |
| 2011/0125157 | A1 | 5/2011 | Sharkey et al. |
| 2011/0125264 | A1 | 5/2011 | Bagga et al. |
| 2011/0125265 | A1 | 5/2011 | Bagga et al. |
| 2011/0125272 | A1 | 5/2011 | Bagga et al. |
| 2013/0035764 | A1 | 2/2013 | Sharkey et al. |
| 2015/0265406 | A1 | 9/2015 | Sharkey et al. |
| 2017/0119529 | A1 | 5/2017 | Sharkey et al. |
| 2017/0273796 | A1 | 9/2017 | Sharkey et al. |

OTHER PUBLICATIONS

"U.S. Appl. No. 13/568,522, Final Office Action dated Jan. 9, 2015", 10 pgs.
"U.S. Appl. No. 13/568,522, Final Office Action dated Mar. 21, 2014", 9 pgs.
"U.S. Appl. No. 13/568,522, Non Final Office Action dated Aug. 5, 2014", 11 pgs.
"U.S. Appl. No. 13/568,522, Non Final Office Action dated Oct. 10, 2013", 13 pgs.
"U.S. Appl. No. 13/568,522, Notice of Allowance dated Apr. 29, 2015", 14 pgs.
"U.S. Appl. No. 13/568,522, Response filed Jan. 10, 2014 to Non Final Office Action dated Oct. 10, 2013", 18 pgs.
"U.S. Appl. No. 13/568,522, Response filed Mar. 9, 2015 to Final Office Action dated Jan. 9, 2015", 11 pgs.
"U.S. Appl. No. 13/568,522, Response filed May 8, 2013 to Restriction Requirement dated Apr. 8, 2013", 2 pgs.
"U.S. Appl. No. 13/568,522, Response filed Jun. 23, 2014 to Final Office Action dated Mar. 21, 2014", 8 pgs.
"U.S. Appl. No. 13/568,522, Response filed Nov. 5, 2014 to Non-Final Office Action dated Aug. 5, 2014", 11 pgs.
"U.S. Appl. No. 13/568,522, Restriction Requirement dated Apr. 8, 2013", 6 pgs.
"U.S. Appl. No. 14/733,334, Notice of Allowance dated Aug. 25, 2016", 8 pgs.
"U.S. Appl. No. 14/733,334, Preliminary Amendment filed Jun. 17, 2015", 7 pgs.
"U.S. Appl. No. 15/359,842, Notice of Allowance dated Mar. 15, 2017", 9 pgs.
"U.S. Appl. No. 15/359,842, Preliminary Amendment filed Jan. 23, 2017", 7 pgs.
"U.S. Appl. No. 15/616,587, Notice of Allowance dated Nov. 3, 2017", 13 pgs.
"U.S. Appl. No. 15/616,587, Preliminary Amendment filed Aug. 18, 2017", 5 pgs.
"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.
"SPU Operative Report. Surgen: Steven B Cohen, M.D.", Treatment of the central medial tibial plateau; A guide pin was inserted into the medial tibial plateau;, An endo button drill bit was used to expand the drill hole; One cubic centimeter (cc) of cement was inserted into the bone; a second drill hole was made from below, and a second cc was inserted into the bone., (Nov. 10, 2008), 4 pgs.
"SPU Operative Report: Surgen Steven B Cohen, M.D.", An Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.

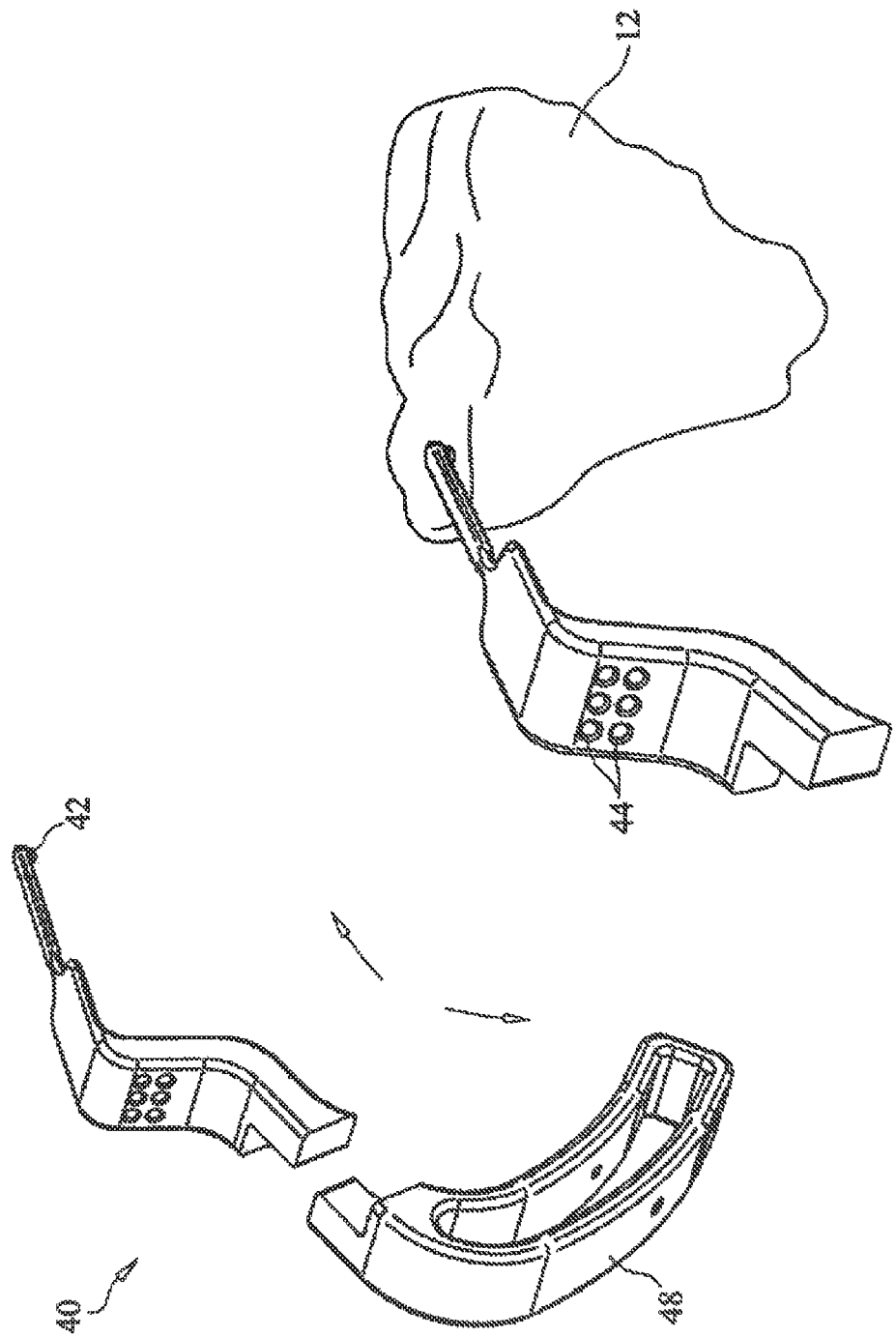

SUBCHONDRAL TREATMENT TO PREVENT THE PROGRESSION OF OSTEOARTHRITIS OF THE JOINT

CROSS-REFERENCE TO RELATED APPLICATIONS

This application is a continuation of U.S. patent application Ser. No. 15/616,587, filed on Jun. 7, 2017, which is a continuation of U.S. patent application Ser. No. 15/359,842, filed on Nov. 23, 2016, which is a continuation of U.S. patent application Ser. No. 14/733,334, filed on Jun. 8, 2015, which is a continuation of U.S. patent application Ser. No. 13/568,522, filed on Aug. 7, 2012, which claims the benefit of priority to U.S. Provisional Application Ser. No. 61/515,953, filed on Aug. 7, 2011 and entitled "Subchondral Treatment to Prevent the Progression of Osteoarthritis of the Joint," which applications are incorporated herein by reference in their entireties.

FIELD

The present invention relates to methods for treating pain resulting from osteoarthritis, and associated devices and instruments for such pain treatment. More particularly, the present invention relates to methods to prevent the progression of osteoarthritis of a joint, by treating the subchondral bone to prevent, or delay the onset or progression of, any bone marrow edema or lesion, along with associated devices and instruments for such subchondral treatment.

BACKGROUND

Osteoarthritis (OA or degenerative arthritis) is the most common joint disorder known. Osteoarthritis is characterized by cartilage loss at the joint, and symptoms generally include pain and stiffness. The disease can affect all joints of the body, including the hip, shoulder, ankle, and spine, to name a few. One form of the disorder, osteoarthritis of the knee, is a common and rapidly growing problem amongst U.S. adults. Knee osteoarthritis often causes severe pain and is associated with loss of function leading to a diminished quality of life. Knee osteoarthritis can be defined by the thinning, softening, fissuring, fibrillation, and eventual loss, of cartilage covering the surface of the bones in the knee joint. In the early stages of the disease process, this loss of cartilage may cause minimal pain and often those afflicted are asymptomatic. Unfortunately, the natural history of knee OA usually is progressive, leading to the significant symptoms and problems already described.

The main goal of osteoarthritis treatments is to reduce or eliminate pain, and restore normal joint function. Both non-surgical and surgical treatments are currently available for this purpose, with the appropriate treatment being selected based in part on the stage and/or severity of the disease.

Non-surgical treatments for knee osteoarthritis include weight loss (for the overweight patient), activity modification (low impact exercise), quadriceps strengthening, patellar taping, analgesic and anti-inflammatory medications, injections, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

One type of surgical treatment focuses on unloading forces from the damaged joint. Another type of surgical treatment aims to replace, either partially or wholly, the damaged area of the joint. For example, one surgical treatment seeks to replace the damaged or worn cartilage by way of cartilage resurfacing or cartilage replacement. Other surgical treatments, such as high tibial osteotomy (HTO) or total knee arthroplasty (TKA), are often recommended for patients with severe pain associated with osteoarthritis, especially when other noninvasive options have failed. Both procedures been shown to be effective in treating knee pain associated with osteoarthritis, at least in the short term.

These treatments are based on the popular theory within the medical community that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. However, the severity of osteoarthritis, especially in the knee, has been found to correlate poorly with the incidence and magnitude of knee pain. Because of this, surgeons and medical practitioners have struggled to deliver consistent, reliable pain relief to patients, especially if preservation of the joint is desired.

One of the most popular treatments for knee OA today is a procedure generally referred to as arthroscopic knee surgery. This type or surgery is frequently used when the patient has associated mechanical symptoms (i.e., locking, clicking, catching, etc.) During an arthroscopic knee surgery, the doctor uses an arthroscope to see inside the knee Joint and do repairs without major surgery. With the arthroscope, the doctor may see early arthritic changes of the articular cartilage and small tears in the meniscus. The tear may be repaired with sutures, staples, or other known tissue fixation devices. Other minor repairs to the cartilage may else be performed in this procedure.

However, it has been observed that patients with osteoarthritis continue to deteriorate and the disease worsens after an arthroscopic knee surgery. It has been observed, in fact that a large proportion of the patients who undergo an arthroscopy of the knee report experiencing worsened pain approximately six months later, with many of these same patients eventually requiring a total knee replacement (TKR). Total knee replacement is a highly invasive, major surgery that is irreversible.

Accordingly, better treatment options are still needed for patients suffering from osteoarthritis to treat the pain and also avoid a total joint replacement surgery. It would be particularly desirable to provide a surgical option that can be performed during an arthroscopic surgery as a preventative step to either stop, or at least delay, the progression of the osteoarthritis symptoms, whereby the surgical option can also alter the natural course of the disease.

SUMMARY

The present disclosure provides methods for the treatment of pain due to osteoarthritis of a joint by treating the subchondral bone, and associated devices and instruments for such subchondral treatment, while preserving, as much as possible, the joint's articular and cartilage surface. One major goal of the methods is to prevent further damage to the bones and joints from the progression of osteoarthritis, by treating the subchondral bone to prevent the manifestation of, delay the onset or progression of, or repair existing, bone marrow edema or lesion in the subchondral space. The methods could be performed before, during, or after an Initial arthroscopic surgery to repair the joint.

In one embodiment, a method for preventing, or slowing the onset or progression of, bone marrow edema in subchondral bone of a joint is provided. The method comprises: conducting a clinical evaluation of the joint and identifying the presence of osteoarthritis in an area of a bone of the joint by the clinical evaluation; creating an access path to a subchondral region of the bone near the area of the osteoarthritis; and treating the subchondral region, via the access path, in a manner that restores normal force distribution and joint function while preserving the articular surface of the bone. The clinical evaluation may be in the form of a physical examination, radiographic imaging (including X-ray imaging), arthroscopic examination, computed tomography imaging (CT scan), ultrasound scanning or imaging (sonography), magnetic resonance imaging (MRI) biochemical imaging, 3-D imaging, or other medical imaging techniques. The osteoarthritis may present as cartilage deterioration, including thinning, softening, fissuring, fibrillation, or loss of cartilage. The treatment may strengthen the bone and/or stimulate the repair of the bone. For example, the treatment may comprise mechanically strengthening the subchondral region of the bone near the osteoarthritis with an implantable device, in another example the treatment may comprise biologically stimulating the subchondral region of the bone near the osteoarthritis with an injectable bone hardening material or other biologically active agent.

In another embodiment, a method for treating osteoarthritis in a joint is provided. The method comprises: conducting a clinical evaluation of the joint and identifying the presence of osteoarthritis in an area of a bone of the joint by the clinical evaluation; creating an access path to a subchondral region of the bone near the area of the osteoarthritis; and treating the subchondral region, via the access path, in a manner that restores more normal force distribution in the subchondral region and joint function while preserving the articular surface of the bone. The clinical evaluation may be in the form of a physical examination, radiographic imaging (including X-ray imaging), arthroscopic examination, CT scan, ultrasound imaging, magnetic resonance imaging, biochemical imaging, 3-D imaging, or other medical imaging techniques. The osteoarthritis may present as cartilage deterioration, including thinning, softening, fissuring, fibrillation, or loss of cartilage. The treatment may prevent the formation, or slow the onset or progression, of a bone marrow edema or lesion in the subchondral region, or the treatment may repair a bone marrow edema or lesion in the subchondral region. The treatment may strengthen the bone and/or stimulate the repair of the bone. For example, the treatment may comprise mechanically strengthening the subchondral region of the bone near the osteoarthritis with an implantable device. In another example, the treatment may comprise biologically stimulating the subchondral region of the bone near the osteoarthritis with an injectable bone hardening material or other biologically active agent.

In still another embodiment, a method for preventing, or slowing the onset or progression of a bone marrow edema in subchondral bone of a joint is provided. The method comprises: conducting an arthroscopic evaluation of the joint and identifying the presence of osteoarthritis in an area of a bona of the joint by the arthroscopic evaluation; creating an access path to a subchondral region of the bone near the area of the osteoarthritis; and treating the subchondral region, via the access path, in a manner that restores normal force distribution and joint function while preserving the articular surface of the bone. The osteoarthritis may present as cartilage deterioration, including thinning, softening, fissuring, fibrillation, or loss of cartilage. The treatment may strengthen the bone and/or stimulate the repair of the bone. For example, the treatment may comprise mechanically strengthening the subchondral region of the bone near the osteoarthritis with an implantable device. In another example, the treatment may comprise biologically stimulating the subchondral region of the bone near the osteoarthritis with an injectable bone hardening material or other biologically active agent.

In yet another embodiment, a method for treating osteoarthritis in a joint is provided. The method comprises: conducting an arthroscopic evaluation of the joint and identifying the presence of osteoarthritis in an area of a bone of the joint by the arthroscopic evaluation; creating an access path to a subchondral region of the bone near the area of the osteoarthritis; and treating the subchondral region, via the access path, in a manner that restores more normal force distribution in the subchondral region and joint function while preserving the articular surface of the bone. The osteoarthritis may present as cartilage deterioration, including thinning, softening, fissuring, fibrillation, or loss of cartilage. The treatment may prevent the formation, or slew the onset or progression, of a bone marrow edema or lesion in the subchondral region, or the treatment may repair a bone marrow edema or lesion in the subchondral region. The treatment may strengthen the bone and/or stimulate the repair of the bone. For example, the treatment may comprise mechanically strengthening the subchondral region of the bone near the osteoarthritis with an implantable device. In another example, the treatment may comprise biologically stimulating the subchondral region of the bone near the osteoarthritis with an injectable bone hardening material or other biologically active agent.

If is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 12-16 illustrate a method of treating a subchondral region of a bone based on another embodiment of the present disclosure.

DESCRIPTION OF THE EMBODIMENTS

Figure 1A:
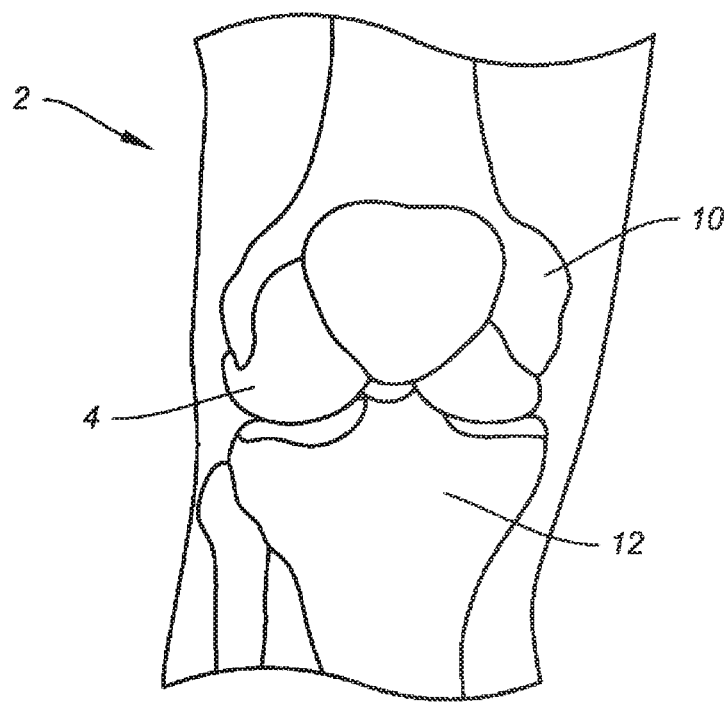
FIGS. 1A and 1B represent exemplary drawings of a healthy knee joint and a knee joint with osteoarthritis and showing cartilage loss, respectively.

Osteoarthritis (OA or degenerative arthritis) is the most common joint disorder known. Although the disease is frequently the subject of clinical studies and research articles, the etiology of the disease, and particularly the source of pain, remains in debate. Knee osteoarthritis, as an example, is believed to be related to a combination of genetic factors, body mass index, activity level, knee alignment (mechanical axis of the leg), and incidence of trauma. Initially, deterioration or loss of cartilage seems to cause minimal pain and the exposed bone usually adapts (by increasing density and strength) to the resulting increased forces. However, when an individual's bone adaptive capacity is exceeded, the resultant damage exceeds the body's ability to repair itself, and thus leads to pain. The onset of pain associated with knee OA is frequently heralded by the presence of subchondral (bone just below the articular surface) defects. These defects may include, for example, a bone marrow lesion (BML) or bone marrow edema (BME), as well as a fissure, fracture, tumor, or sclerotic hardening.

An edema is a phenomenon identifiable by magnetic resonance imaging (MRI), especially using T2 weighted MRI techniques. A BME represents an inflammatory response in overstressed bone that has been excessively damaged beyond an individual's reparative capacity. It has been observed that knee OA progresses more rapidly, with accelerated loss of cartilage, when BME is present. This acceleration likely occurs because the damaged and inflamed subchondral bone does not optimally support the remaining overlying cartilage in the knee joint.

With the onset of knee OA, early cartilage thinning, softening, fissuring, fibrillation, or loss of articular cartilage may be asymptomatic and incidentally identified by any number of clinical evaluation methods, including physical examination, plain radiographs (x-ray), CT scan, ultrasound, MRI, biochemical imaging, 3-D imaging, or arthroscopy. An intervention at this early stage of the disease, that aims to strengthen subchondral bone and/or enhance its reparative capacity, is predicted to change the natural history of the joint and etiology of knee OA. Thus, a delay or prevention of the manifestation of BME will positively affect the time at which knee OA pain develops. Maintaining subchondral bone strength will also lead to improved support of the remaining articular cartilage. This improved support will slow the deterioration of the remaining cartilage.

Currently, the most popular surgical treatment for osteoarthritis, particularly when mechanical symptoms (i.e., clicking, locking, catching, etc.) are present, is arthroscopy, a surgical procedure in which the doctor uses an arthroscope to see inside the joint and make minor repairs. With the arthroscope, the doctor may see early arthritic changes of the articular cartilage and small tears in the meniscus. The tear may be repaired with sutures, staples, or other known tissue fixation devices. Other minor repairs to the cartilage may also be performed in this procedure.

As previously mentioned, in many cases after an arthroscopy, the patient continues to deteriorate and the disease worsens due to the progression of OA. Further, a large proportion of the patients who undergo an arthroscopy report experiencing worsened pain approximately six months later, with many of these same patients eventually requiring a total joint replacement.

This disclosure offers one theory to explain this trend: the actual mechanical disruption to the joint caused by the interventional arthroscopic procedure itself, in fact, exacerbates a pre-existing defect that is part of an underlying root cause of the pain (which may or may not be immediately detectable), which defect resurfaces to a greater extent down the road, leaving the patient with no other viable alternative but a total joint replacement, a highly invasive and non-reversible surgery. A great deal of stress and force must be exerted on the joints during an arthroscopy to create sufficient space between the gaps of the joint to allow for the repair. This stress would aggravate an already existing stressed defect, such as an impending or actual stress fracture, within the bone that induces a worsening of the condition of the subchondral bone, or promote the formation of other defects including bone hardening (sclerotic bone), bone marrow edema or lesion, for example. These defects lead to the progression of the OA and eventual increased pain and decreased joint function. Another theory is that the natural history of OA is progressive and subchondral bone forces continually increase as a result of this progression.

A method for altering OA's natural history and slowing disease progression is proposed. A technique, SUBCHONDROPLASTY™ or SCP™, for repairing damaged subchondral bone associated with knee OA has previously been described in U.S. application Ser. No. 12/950,355 by applicants. SCP™ has proven to predictably relieve knee OA pain and improve patient reported quality of life. SCP™ is a unique intervention allowing for the repair of damaged subchondral bone without violating the articular surface of the joint. Resolution of BME has been shown to slow knee OA progression.

The current proposed methods apply the SCP™ techniques developed by applicants in a prophylactic manner. Preventive SCP, or PSCP, is intended to prevent the manifestation of any bone marrow edema or bone marrow lesion in the subchondral bone, which as previously described is one of the underlying root causes for joint pain and the progression of OA in a joint. These methods involve accessing, repairing, enhancing, and/or stimulating subchondral bone in the region below and/or adjacent to the articular surface where cartilage deterioration, thinning or complete loss of cartilage is identified. These methods prevent bone marrow edema from manifesting in subchondral bone, ultimately treating the OA itself by preventing or delaying the disease progression. Further, the methods may be used before, during or after arthroscopic treatment as a preventative measure to inhibit the progression of the disease.

The disclosed methods restore natural joint function while preserving, as much as possible, the joint's articular and cartilage surface. Treatments through the joint that violate the articular and cartilage surface often weaken the bone and have unpredictable results. Rather than focusing on treatment through the joint, the embodiments treat the subchondral region of a bone of a joint to prevent bone marrow edema end treat osteoarthritis by inhibiting its progression. Of course, in some cases where bone marrow edema may be present but not yet identified, it is understood that the treatments disclosed are suited for treating the existing bone marrow edema as well as preventing them.

Each of the PSCP methods disclosed are based upon the discovery that pain associated with osteoarthritis joints can be correlated to bone defects or changes at the subchondral level rather than, for example, the severity of osteoarthritic disease or defects at the articular surface level. In particular, bone defects, such as bone marrow lesions, edema, fissures, fractures, hardened bone, etc. near the joint surface lead to a mechanical disadvantage and abnormal stress distribution in the subchondral bone, which may cause Inflammation and generate pain. By altering the makeup of the subchondral bone (which may or may not be sclerotic) in relation to the surrounding region, it is possible to change the structural integrity of the affected bone and restore normal subchondral force transmission and/or stimulate bone repair, thus leading to a delay or prevention of OA symptoms and/or OA progression.

Treatment of the bone by mechanical and/or biological means to restore the normal physiologic stress distribution, and restore the healing balance of the bone tissue at the subchondral level, is a more effective way of treating pain than conventional techniques. That is, the treatment can be effectively achieved by: (a) mechanically strengthening or stabilizing the subchondral bone; (b) biologically initiating or stimulating a healing response in the subchondral bone to a stressed defect, such as, for example, an impending or actual stress fracture; or (c) both (a) and (b) combined. According, the present disclosure provides methods, devices, and systems for a subchondral procedure.

The PSCP subchondral techniques disclosed herein apply previously described SCP™ methods as prophylactic measures to prevent or delay the progression of OA in joints. Like SCP™, the preventive form of SCP™, or PSCP, endeavors to treat the subchondral bone by: (a) mechanically strengthening or stabilizing the subchondral bone; (b) biologically initiating or stimulating a healing response in the subchondral bone; or (c) both (a) and (b) combined. By doing so, PSCP aims to prevent the manifestation of BME's and other subchondral defects in the subchondral bone, which defects can lead to the progression of the OA and eventual increased pain and decreased joint function. Further, PSCP alters the natural progressive history of OA, preventing subchondral bone forces from continually increasing by inhibiting the disease's progression. PSCP can be carried out using the same devices, instruments and systems for SCP™ that are marketed under the registered trademark name of SUBCHONDROPLASTY™.

In general, PSCP methods are similar to the SUBCHONDROPLASTY™, or SCP™, techniques and are intended to both strengthen the bone and stimulate the bone. As with SCP, in preventive SCP or PSCP bone fractures or non-unions are stabilized, integrated or healed, which results in repair and/or resolution of a bone defect, such as a bone marrow lesion or edema. In addition, PSCP restores or alters the distribution of forces in a joint to thereby relieve pain. PSCP can be performed arthroscopically or percutaneously to treat a stressed fracture, preventing the manifestation of any bone marrow lesion or edema during the progression of the OA, and preserving, as much as possible, the articular surfaces of the joint.

PSCP methods involve the steps of clinically evaluating a joint by any of the methods previously described, defecting the presence of osteoarthritis in a bone of the joint, accessing the subchondral region of the bone near the area of osteoarthritis, and treating the subchondral region to restore normal force distribution and joint function while preserving the articular surface of the bone. Further clinical evaluation can be performed to determine the extent of treatment of the subchondral region. The present disclosure provides several exemplary treatment modalities for PSCP for the different extents of treatment needed. Accordingly, a medical practitioner may elect to use any of the techniques and devices described herein, either alone or in combination, to subchondrally treat the subchondral bone as be deems appropriate.

Initially, a clinical evaluation of the patient's joint is necessary to determine the extend and the location of the osteoarthritis. This clinical evaluation can comprise a physical examination or an arthroscopic examination (i.e., during an arthroscopy). Of course, as previously mentioned, other types of medical imaging techniques can be used to evaluate the joint, including radiographic imaging (plain X-ray), computed tomography imaging (CT scan), ultrasound scanning or imaging (sonography), magnetic resonance imaging (MRI), biochemical imaging (e.g., T2 mapping, T1rho imaging, sodium MRI, and delayed gadolinium-enhanced MRI of cartilage or dGEMRIC), 3-D imaging, or other medical imaging techniques. The goal of the evaluation is to identify the cartilage degeneration (e.g., thinning, softening, fissuring, or fibrillation) or cartilage loss in a joint with OA, and consequently the severity or stage of the disease.

The severity of the OA of a joint can be characterized by the following Table 1 which provides an arthroscopic classification of the severity of OA or level of cartilage damage that has been accepted by the medical community. Generally speaking, the present PSCP methods are well suited for administration to a bone of a joint exhibiting Grade III or IV osteoarthritic conditions. However, it is understood that the present methods may equally be applied in cases of Grade I and II OA conditions, if very early prevention is so desired. Thus, the proposed PSCP methods are intended to be used in any patient with OA (Grades I through IV), identified in the joint by recognition of cartilage degeneration, thinning or loss by any of the known identification methods already mentioned (e.g., plain radiographs, x-ray, CT scan, ultrasound, MRI, biochemical imaging, 3-D imaging, arthroscopy, etc.)

TABLE 1

Arthroscopic Classification of Severity of OA

| Grade | Description |
|---|---|
| 0 | Normal; healthy cartilage |
| 1 | Swelling and softening of cartilage; edema or cellular infiltrate - the cartilage has soft spots or blisters |
| 2 | Superficial fibrillation - minor tears in the cartilage |
| 3 | Deeper and large cartilage fibrillation/fissuring - lesions have deep crevices (more than 50% of cartilage layer) |
| 4 | Visualization of underlying subchondral bone - the cartilage tear exposes the underlying bone |

As previously stated, the present PSCP methods focus on the treatment of the subchondral bone of a joint that manifests osteoarthritis conditions or early cartilage damage. An intervention at this early stage of the disease, that aims to strengthen subchondral bone and/or enhance its reparative capacity, is predicted to change the natural history of the joint and etiology of the disease. PSCP methods aim to delay or prevent the manifestation of BME, which is believed to positively affect the time at which OA pain develops. In addition, maintaining subchondral bone strength will also lead to improved support of the remaining articular cartilage. This improved support will slow the deterioration of the remaining cartilage.

One of the advantages the present PSCP methods offer is that the positive identification of a subchondral detect (e.g., an existing BME or BML) is not required prior to performing the method. It is known that a bone marrow lesion or bone marrow edema (BML or BME) can be detected by imaging, e.g., magnetic resonance imaging (MRI), X-ray, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging certain defects may be identified.

But for any number of reasons, these detects may not be identified before or during an arthroscopy. For instance, the radiologist may not be looking for these particular defects, or the sequence of MRI's is not appropriate for this type of defect detection. Still in another example, the imaging simply does not pick up any defect under the arthritic damage. This could be the case where the imaging is not sensitive enough to identify early subchondral bone damage. By not requiring the positive identification of subchondral damage, the methods of the present disclosure can be widely implemented without the additional burden of imaging requirements. Detection of early arthritic changes of the articular cartilage is sufficient for the present methods. And, equally advantageous, the methods can be practiced alongside an arthroscopy, a very common procedure performed on patients with early stage OA.

Another advantage of PSCP methods is that they allow for additional treatments to continue after they are performed. For example, these PSCP treatments may be performed in conjunction with other procedures, such as cartilage resurfacing, regeneration or replacement, if desired. Of note, if needed, the patient may continue to have a joint replacement or other type of procedure since the PSCP procedure does not interfere with a joint replacement or other type of procedure.

The present methods provide a number of treatment modalities, and associated devices, instruments and related methods for treating the subchondral bone. These treatment modalities may be used alone or in combination. The ultimate goal of these modalities is to restore mechanical stability to the subchondral bone below or adjacent the area of the osteoarthritis. In untreated subchondral bone below the arthritic damage, an already stressed defect, such as an impending or actual stress fracture, becomes aggravated as the disease progresses and results in the formation of other, more severe defects like BME's. PSCP methods aim to prevent the manifestation of BME's and other subchondral defects in the subchondral bone, which defects can lead to the progression of the OA and eventual increased pain and decreased joint function. Further, PSCP alters the natural progressive history of OA, preventing subchondral bone forces from continually increasing by inhibiting the disease's progression.

In one treatment modality, the subchondral bone under the arthritic condition can be strengthened by the introduction of a hardening material, such as a bone substitute, in the localized region. In some instances, some of the soft bone tissue in the localized region of the subchondral bone is compacted prior to insertion of the hardening material. The bone substitute may be an injectable calcium phosphate ensconced in an optimized carrier material. In some cases, the injected material may also serve as a bone stimulator that reinvigorates the bone's natural repair and healing activity.

For example, polymethylmethacrylate (PMMA) or calcium phosphate (CaP) cement injections can be made at the subchondral localized region. PMMA injection may increase the mechanical, strength of the bone, allowing it to withstand greater mechanical stresses. CaP cement injection may also increase the mechanical strength of the bone, white also stimulating the localized region for bone fracture repair.

In another treatment modality, the subchondral bone below or adjacent the arthritic damage can be stimulated to trigger or improve the body's natural healing process. For example, in one embodiment of this treatment modality, small holes may be drilled at the localized region of the subchondral bone to increase stimulation (e.g., blood flow, cellular turnover, etc.) and initiate bone repair. In another embodiment, after holes are drilled an osteogenic, osteoinductive, or osteoeonductive agent may be introduced to the localized region of the subchondral bone. In addition, some of the bone tissue may be compacted in order to assist in stimulating the bone tissue or create space for the introduction of bone graft material. Bone graft material, for example, may be used to fill the hole. This treatment modality may create a better load-supporting environment leading to long term healing. Electrical or heat stimulation may also be employed to stimulate the healing process of a chronically injured bone. Chemical and bio-chemical stimulation may also be employed. Moreover, stimulation of bone tissue may be enhanced via the use of cytokines and other cell signaling agents to trigger osteogenesis, chondrogenesis, and/or angiogenesis to perhaps reverse the progression of osteoarthritis.

In yet another treatment modality, an implantable device may be implanted into the localized region of the subchondral bone below or adjacent to the arthritic damage to provide mechanical support to the localized bone region, particularly where an insufficiency fracture or stress fracture is present. In some embodiments, some of the bone tissue may be compacted in order to create space for the implantable device. The implant may help create a better load distribution in the subchondral region. In knees, the implant may support tibio-femoral compressive loads. In addition, the implant may mechanically integrate with the surrounding healthy bone tissue. The implant may be placed in cancellous bone, through sclerotic bone, or under sclerotic bone at the affected localized region. The implant may also be configured as a uni-cortical or bi-cortical bone implant. The implant may be inserted using a guide wire. In one example, the implant may be inserted over a guide wire. In another example, the implant may be delivered through a guide instrument. The guide instrument may be used to enter a desired access path that is determined using a mapping system that provides a set of coordinates for targeting the location of the subchondral region. Such a mapping system may be similar to the one disclosed in co-pending and co-owned U.S. patent application Ser. No. 12/950,114, filed Nov. 19, 2010 and entitled "Coordinate Mapping System for Joint Treatment," the contents of which are herein incorporated in their entirety by reference.

The implant may further be augmented with a PMMA or CaP cement injection, other biologic agent, or an osteoeonductive, osteoinductive, and/or osteogenic agent. The augmentation material may be introduced through the implant, around the implant, and/or apart from the implant but at the affected localized bone region. In addition, the implant may also serve as a portal to inject the augmentation material into the subchondral bone region.

While each of the above-mentioned treatment modalities may be administered independent of one another, it is contemplated that any combination of these modalities may be applied together and in any order so desired, depending on the severity of the OA. Accordingly, the present disclosure also provides suitable implantable fixation devices for the surgical treatment of these localized bone regions of the subchondral bone. Also provided are devices and instruments that can be used in combination with cements or hardening materials commonly used to repair damaged bone by their introduction into or near the localized region of the subchondral bone of damage, either to create a binding agent, cellular scaffold or mechanical scaffold for immobilization, regeneration or remodeling of the bone tissue.

Figure 1B:
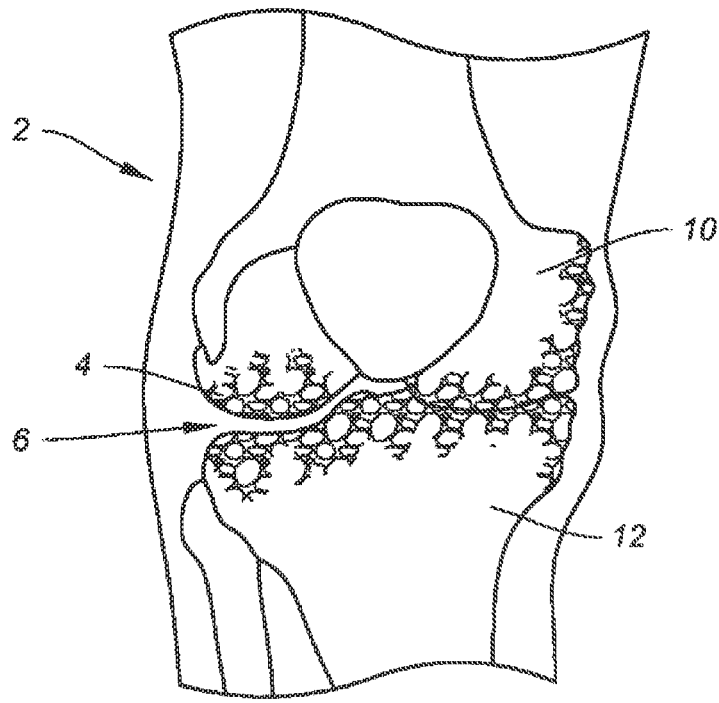

As notes, embodiments of the present disclosure may be explained and illustrated with reference to treatment of a patient's knee, though it is understood that the devices, instruments and methods of the present disclosure may be applicable to other joints as well, such as the shoulder, hip, spine, and ankle. Referring now to FIG. 1A, a healthy human knee 2 comprising a femur 10 and a tibia 12 is shown. The articular cartilage 4 appears smooth and healthy, and does not show any damage or loss. In contrast, FIG. 1B shows an osteoarthritic knee. The articular cartilage 4 shows signs of degradation, and in between the joint there is cartilage loss 6. Typical arthritic damage like that shown in FIG. 1B would be deniable through a clinical evaluation of the knee joint 2, such as by physical examination, radiographic imaging (including X-ray imaging), arthroscopic examination, CT scan, ultrasound imaging, magnetic resonance imaging, biochemical imaging (e.g., T2 mapping, T1rho imaging, sodium MRI, and delayed gadolinium-enhanced MRI of cartilage or dGEMRIC), 3-D imaging, or other medical imaging techniques. After a clinical evaluation of the arthritic condition of the joint is performed, and cartilage damage or loss is identified, the PSCP methods of the present disclosure may be performed.

As previously mentioned, PSCP methods employ one or more treatment modalities to address the subchondral bone. In one treatment modality, the subchondral bone under the arthritic condition can be strengthened by the introduction of a hardening material, such as a bone substitute, in the localized region. In another treatment modality, the subchondral bone below or adjacent the arthritic damage can be stimulated to trigger or improve the body's natural healing process. In yet another treatment modality, an implantable device may be implanted into the localized region of the subchondral bone below or adjacent to the arthritic damage to provide mechanical support to the localized bone region.

Figure 2A:
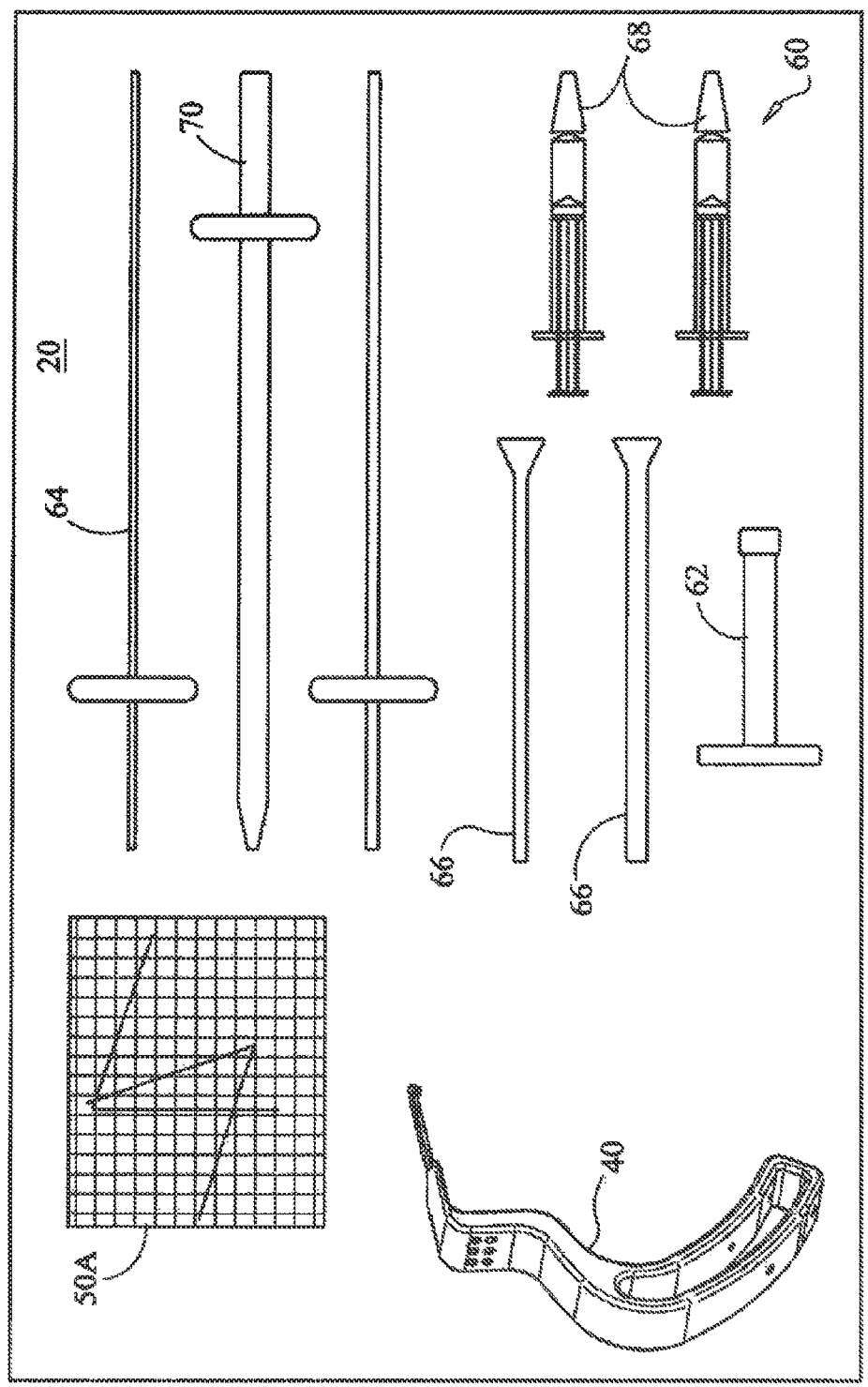
FIGS. 2A and 2B show exemplary instrument systems for carrying out the methods of the present disclosure.
Figure 2B:
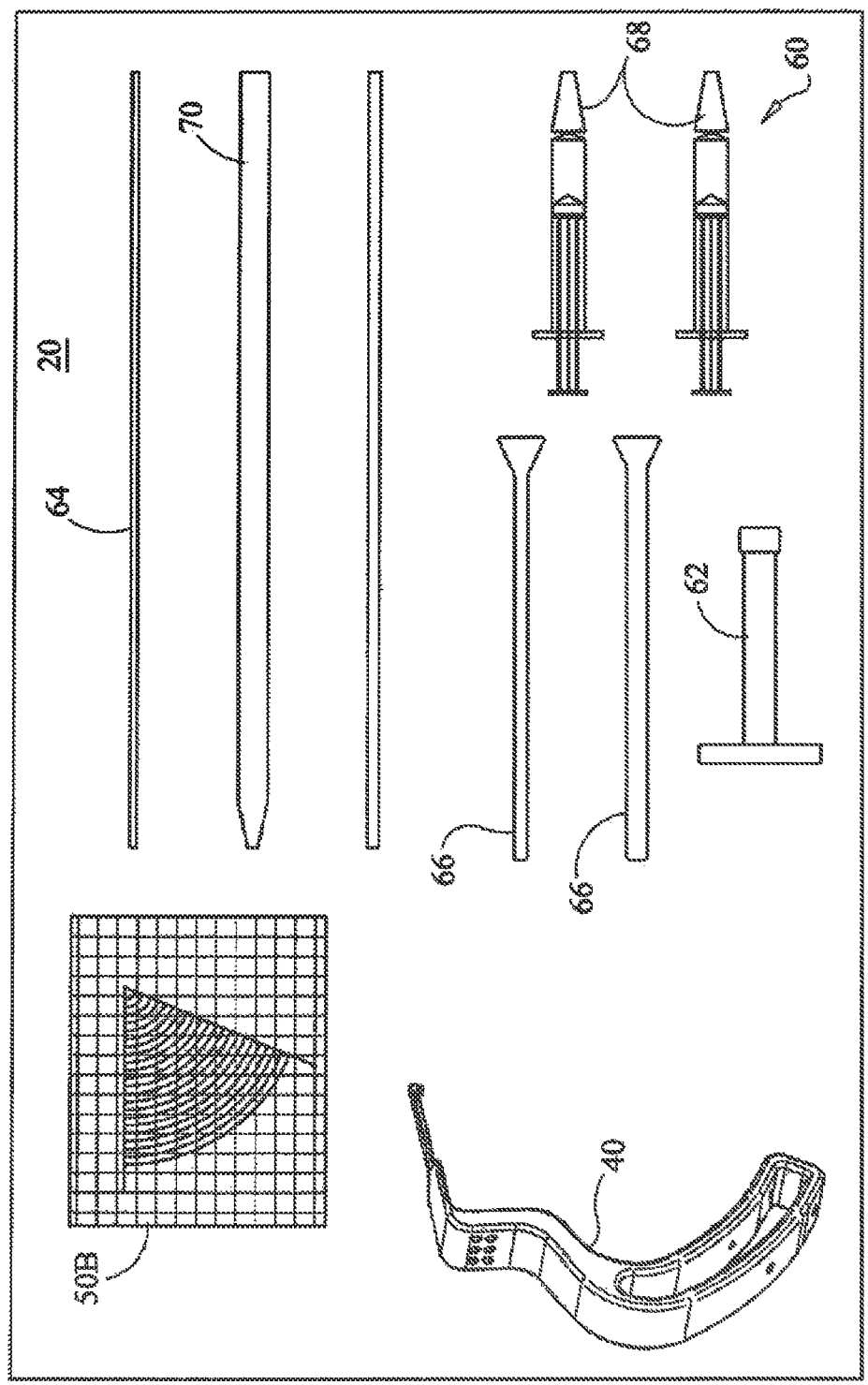

FIGS. 2A and 2B show exemplary instrument systems 20 useful for implementing one or more of these treatment modalities. These instrument systems 20 are provided for facilitating the injection of a treatment material such as a bone hardening material or a bone void filler into subchondral space. As shown, the components of the instrument system may include, among other things, a guide/insertion instrument 40, templates 50A, 50B, and various tools 60 for assessment and/or drilling. For example, the tools 60 provided in Instrument system 20 may include a volume assessment tool, a fixed bone portal 62, a Kirschner wire (or K-wire) 64, a bore creation device, several injection catheters 66 sized to match the bore creation device, several syringes 68, and a portal hole plug. In some embodiments, the instrument systems 20 are provided to surgeon or medical facility pre-packaged and sterile. In addition, some or all of the instruments and tools provided in the instrument system 20 may be reusable or disposable.

The instrument systems 20 may also include a cavity creation device (not shown in FIGS. 2A and 2B). Cavity creation devices may include burrs, punches, reamers, rongeurs, tamps, drills 70, instruments with expandable components, such as balloons, stents or looped wires, instruments with a selectively angulatable or reconfigurable distal ends, and others known in the art.

Additionally, the instrument system 20 can include an assortment of implantable devices or reinforcing members (not shown) of various sizes and/or shapes appropriate for use with a variety of bone shapes and sizes. The instrument system 20 can also include instructions for use, e.g., printed on the container and/or on inserts within the container. The instrument system 20 can still further include a tool for adjusting the size of the reinforcing member, a hammer for driving the reinforcing member into the bone and/or a bone filler to seal the open end of the channel in the bone in which the reinforcing member resides. As noted, the instrument system 20 may be prepackaged and sterile with an assortment of reusable or disposable instruments and tools.

Suitable bone fillers include but are not limited to materials comprising beta-tricalcium phosphate (e.g., VITOSS, PROOSTEON 500R made by E-Interpore-Cross International), hydroxyapatile (e.g., OSTEOGRAF made by Ceramed Denta, Inc. Lakewood, Colo.), calcium carbonate, calcium sulfate (e.g., OSTEOSET and ALLOMATRIX made by Wright Medical Technology. Inc.), calcium phosphate (e.g., CALCIBON made by Merck & Co., Inc., Whitehouse Station, N.J. and NORIAN SRS made by Synthes-Strates, Switzerland), synthetic bone fillers (e.g., CORTOSS) and/or processed bone fillers (e.g., BIOOSS made by Geistlich Biomaterials, Inc., Switzerland). Other suitable materials may include hydrogels, PEEK (polyetheretherketone), carbon fiber polycarbonate urethane (PCU), stem cells with and without matrices, collagen with and without matrices and carriers, pharmacotherapeutic with and without matrices and carriers, hyaluronic acid with and without matrices, in situ curable materials with and without anti-inflammatory agents, demineralized bone matrix, allograft, biocompatible metals, resorbable PCA, PGLA, and polyurethane, hydroxyapatite, calcium sulfate, BMP growth factor, TGF-β super family, MP52, TP508, bioactive glass, sodium alignate, AOC based carrier and active components (synthetic beeswax), and starch.

In some embodiments, the bone filler may be of a type that can expand upon insertion. For example, the filler may be injectable at the localized region of the subchondral bone, whereupon it can fill up or expand into the region. If desired, the bone void filler may also be implanted in a step-wise fashion such that an initial stage to establish primary fixation is followed with a subsequent stage of assembly that provides added strength and bone integration properties to the fully assembled bone void filler.

As shown in FIG. 2B, another embodiment of the instrument system 20 can include a fluid, a syringe for injecting the fluid into a bone and a container adapted to maintain the sterility of the contents of the container. As noted, the instrument system 20 may be prepackaged and sterile with an assortment of reusable or disposable instruments. This embodiment of the instrument system 20 can further comprise a needle and premeasured portions of ingredients in a plurality of separate vials. As with the first embodiment of the instrument system 20, this embodiment can optionally include instructions for use, e.g., printed on the container and/or on inserts within the container. The instrument system 20 can further include bone tools for providing a channel in the bone in which the fluid is injected and or a bone filler to seal the open end of the channel in the bone in which the reinforcing member resides.

The instrument system 20 can further include curing agents (i.e., polymerizing agents, catalysis and/or cross linking agents) as separate ingredients to be added to the injected fluid. The instrument system 20 can include other curing means, such as a UV light source or other device for generating radiation. The fluid can be preloaded in the syringe for injection. In some embodiments, a multiple barrel syringe can be included for in situ mixing of ingredients that must be stored separately in different barrels of the syringe (e.g., monomers and polymerizing agent, or polymers and cross linking agent, etc.).

Figure 3A:
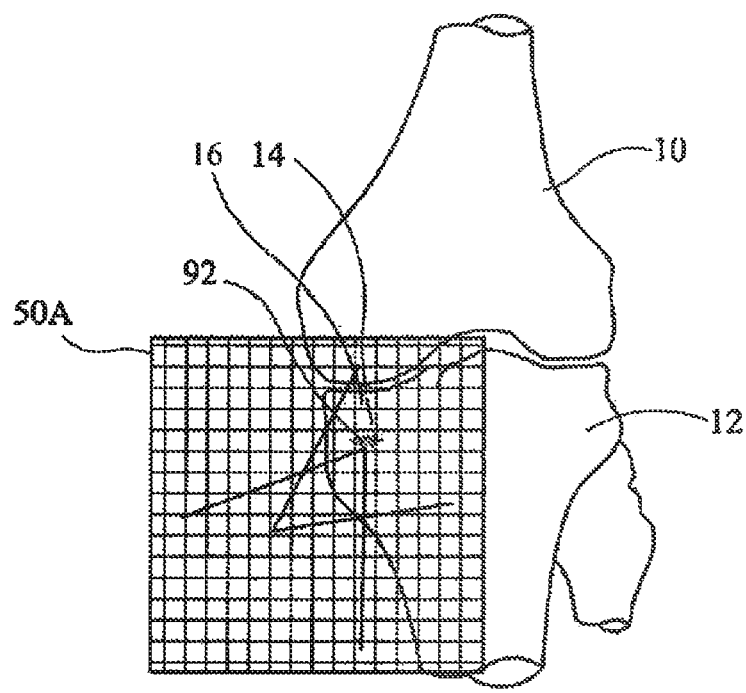
FIG. 3A shows a template of the system of FIG. 2A in use.
Figure 3B:
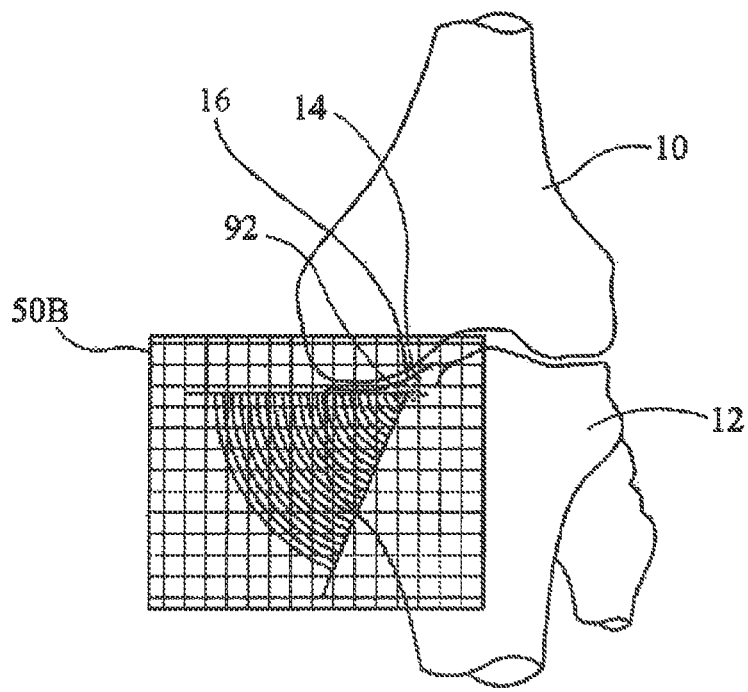
FIG. 3B shows a template of the system of FIG. 2B in use.

FIG. 3A shows a template 50A of the instrument system 20 from FIG. 2A in use. FIG. 3B shows a template 50B of the instrument system 20 from FIG. 2B in use. As part of the pre-operative planning process, medical imaging, such as an MRI illustrated in FIG. 1, is taken of the knee of a patient suffering from arthritic pain. For purposes of clarity, FIGS. 3A and 3B show the templates 50A, 50B overlaying a simplified illustration of a knee. These templates may be useful in situations where imaging of the joint has occurred, and a localized region 92 of the subchondral bone 14 below an area of articular cartilage damage or loss 16 has been identified and located by the imaging, such as by MRI. The approximate size, volume and orientation are determined from the image, and based on the values, the recommended volume of bone void filler is determined from the volume assessment tool.

The templates 50A and 50B, shown in FIGS. 3A and 3B, may be a transparent to indicate how the localized region 92 can be treated. In use, for example, the templates 50A and 50B are placed over the MRI image to determine the placement of the guide/insertion instrument 40, the appropriate location for a bone portal 62, and the resulting depth to the localized region 92.

Figure 4A:
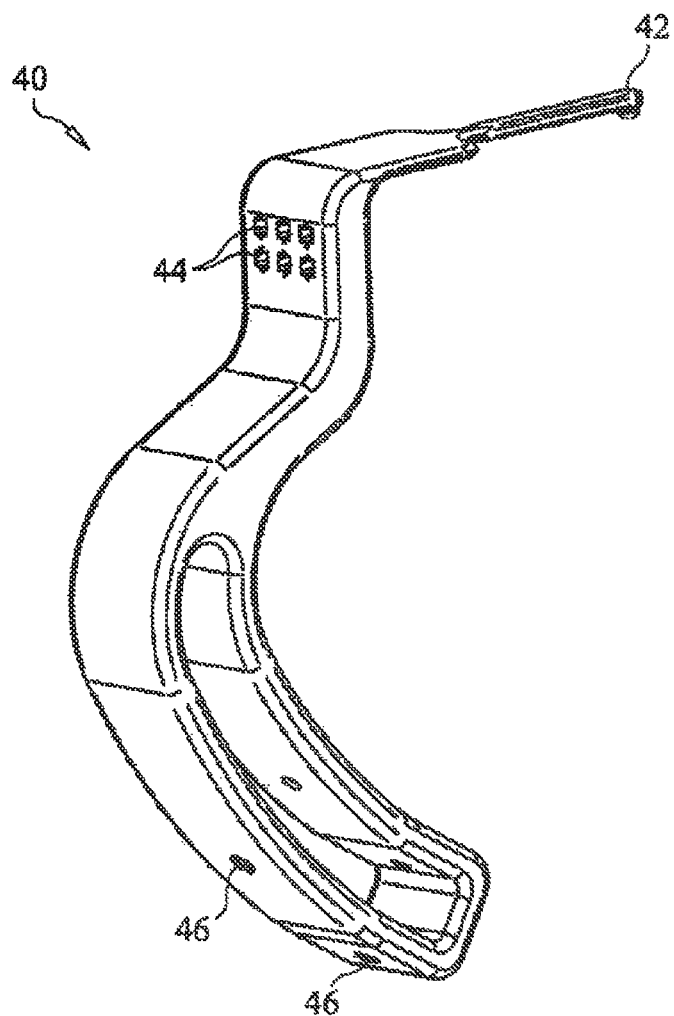
FIG. 4A shows an exemplary embodiment of a guide/insertion tool or instrument of the present disclosure.

FIG. 4A shows an exemplary embodiment of a guide/insertion instrument 40. As shown, the guide/insertion instrument 40 may comprise an integrated cartilage reference 42, a parallel drill/implant guide 44, and angular drill guide/portal 46

The guide/insertion instrument 40 is included in the instrument system 20 to aim the bone portal 62 and to set the depth stop of drilling for the surgeon. As shown, the guide/insertion instrument 40 may comprise a curved body, a probe, and an optional adjustable arm (not shown). The curved body has a radius of curvature that provides for different angles of approach to the tip of the probe. The probe is attached to the curved body and may have a planar, rasped tip for contacting and gripping the articular surface of the knee joint without damaging the cartilage. The optional adjustable arm (not shown) may be connected to the curved body through a sliding arrangement such that the angle of the arm is adjustable with respect to the curved body.

Figure 4B:
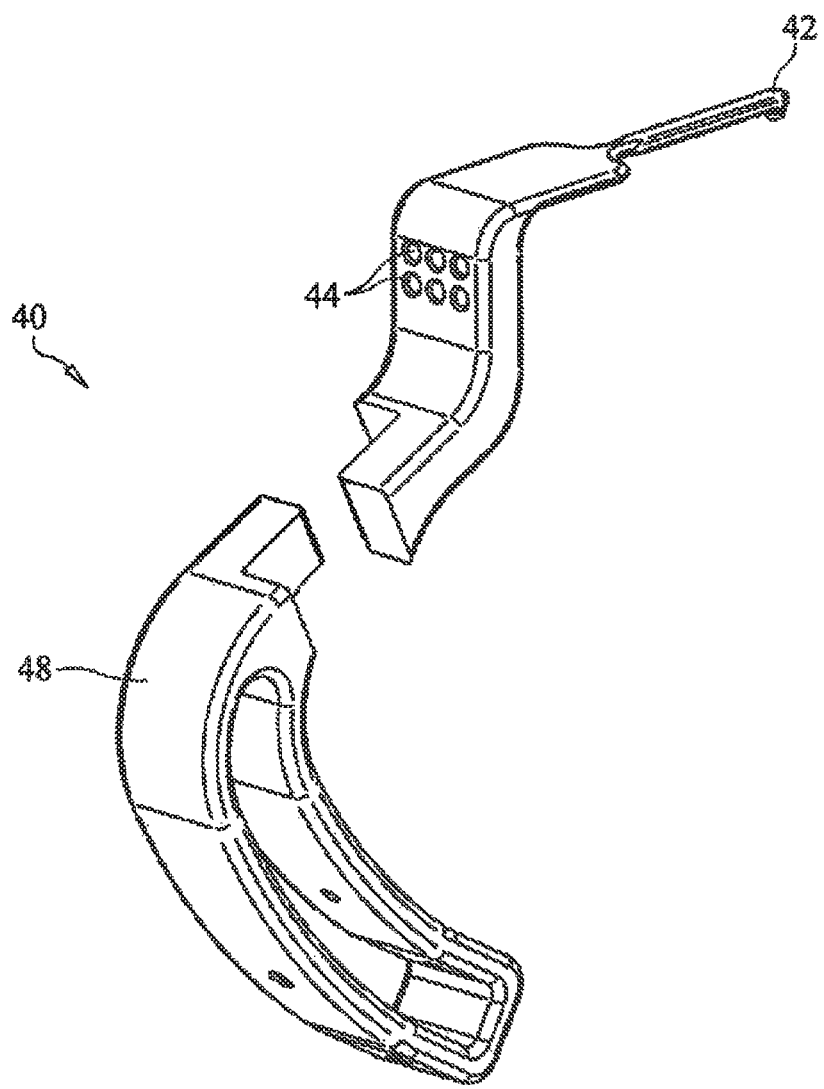
FIG. 4B shows another exemplary embodiment of a guide/insertion tool or instrument of the present disclosure.

FIG. 4B shows another exemplary embodiment of the guide/insertion instrument 40. As shown, in this embodiment, the guide/insertion instrument 40 may comprise a detachable handle 48. The detachable handle 48 may be detachable in order to facilitate its manipulation during surgery. The detachable handle 48 may be detachable based on various mechanisms that are known to those skilled in the art.

Figure 5:
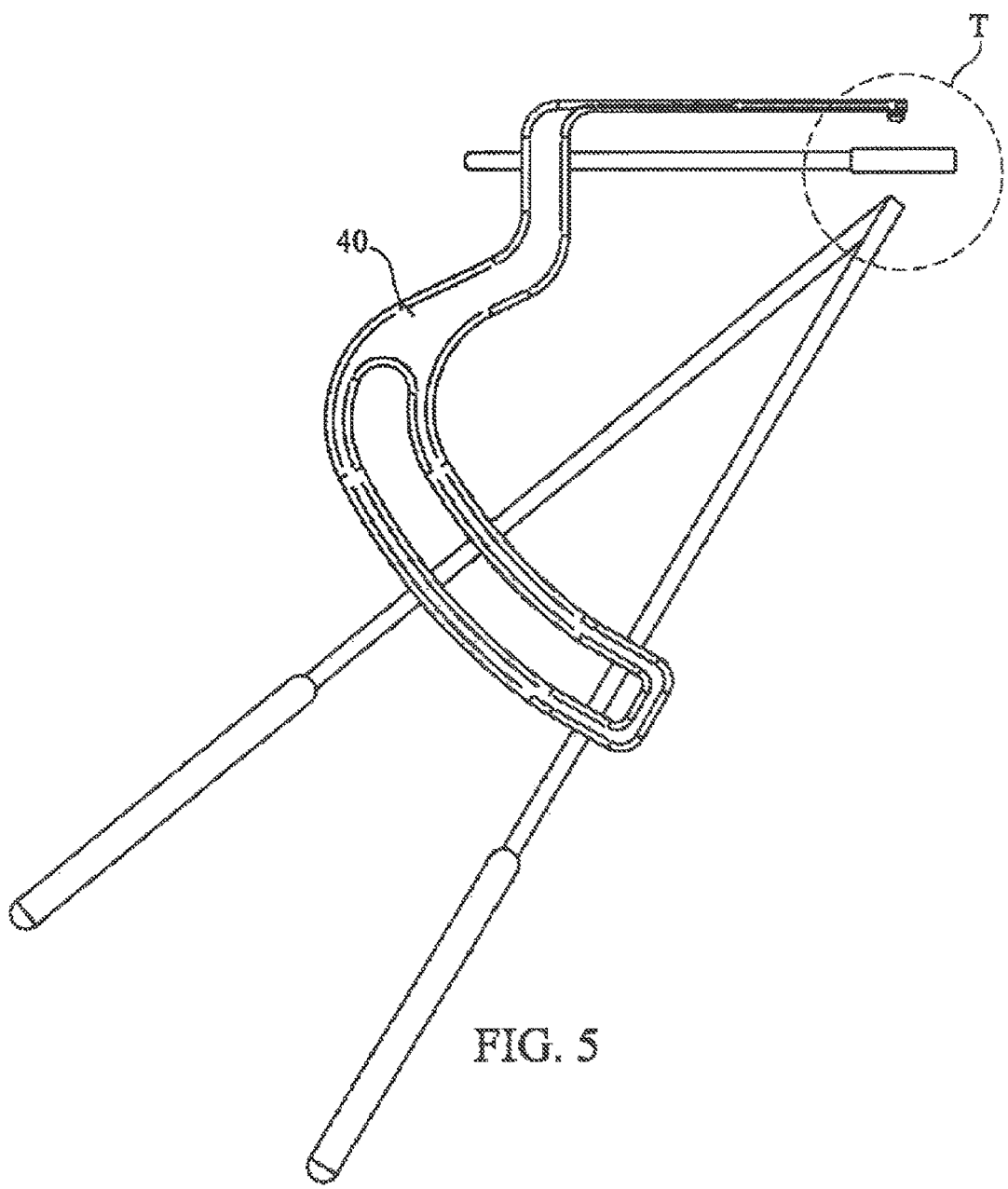
FIG. 5 illustrates a side view of a guide/insertion instrument and various features of the guide/insertion instrument in use with other instruments of the system.

FIG. 5 illustrates a side view of the guide/insertion instrument 40 and various options of the instrument 40. As shown, the probe of the guide/insertion instrument 40 may comprise integrated cartilage reference 42 and parallel drill/implant guide 44. The guide 44 is configured to guide a drill 70 or other tool to a location or target T indicated by the cartilage reference 42. In addition, in the embodiment shown, the curved body of the guide/insertion instrument comprises an angular drill guide/portal 46. The guide/portal 46 may provide a set of guides/portals that converge at location T from various angles, such as 30 degrees and 45 degrees.

Figure 6:
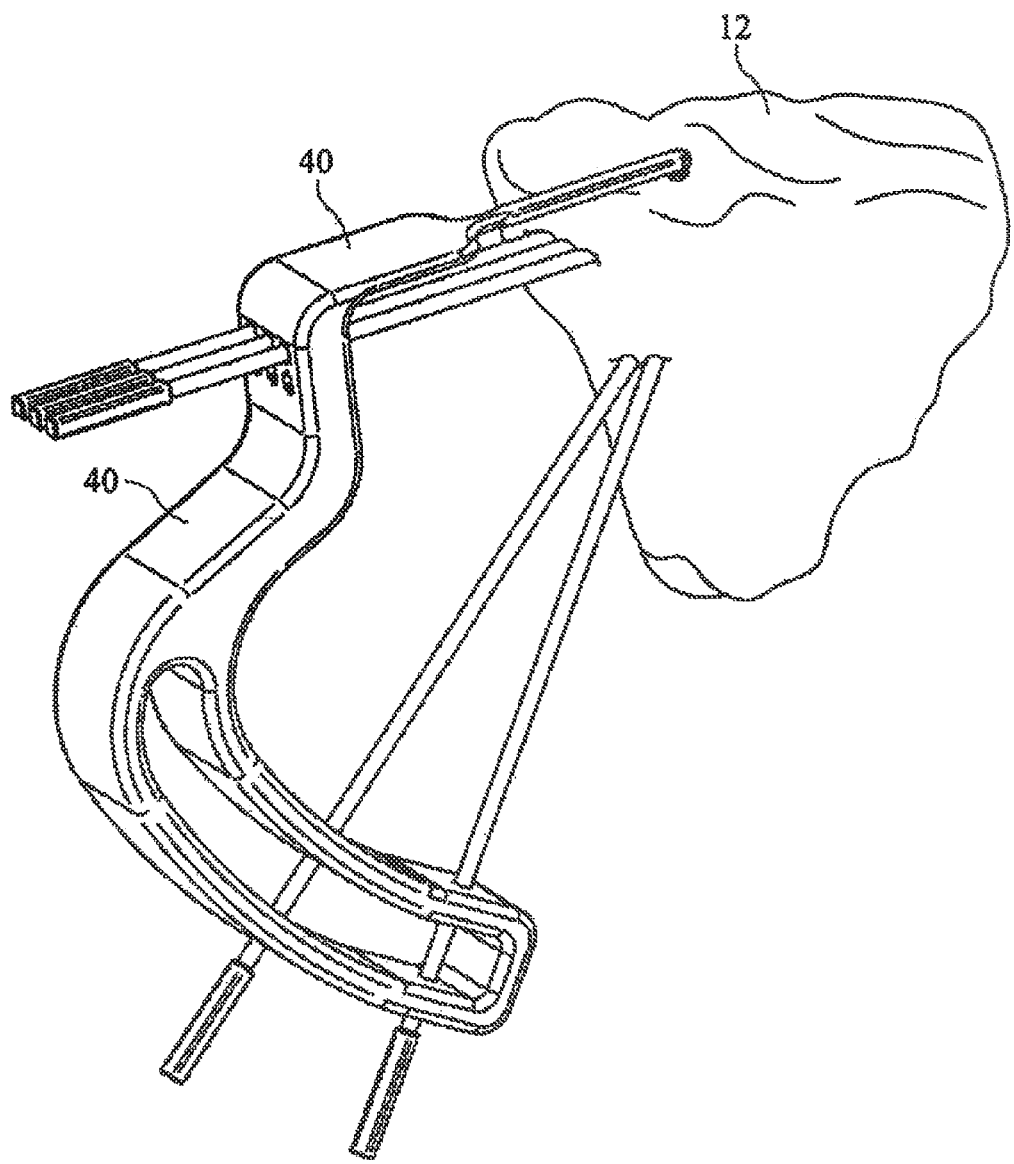
FIG. 6 illustrates a perspective view of the various features of the guide/insertion instrument in use with other instruments or the system.

FIG. 6 illustrates a perspective view of the various options of the guide/insertion instrument 40. As shown, the parallel drill/implant guide 44 may comprise a series of holes/portals in a matrix configuration to help guide a drill 70 or other tool to location T.

Figure 7A:
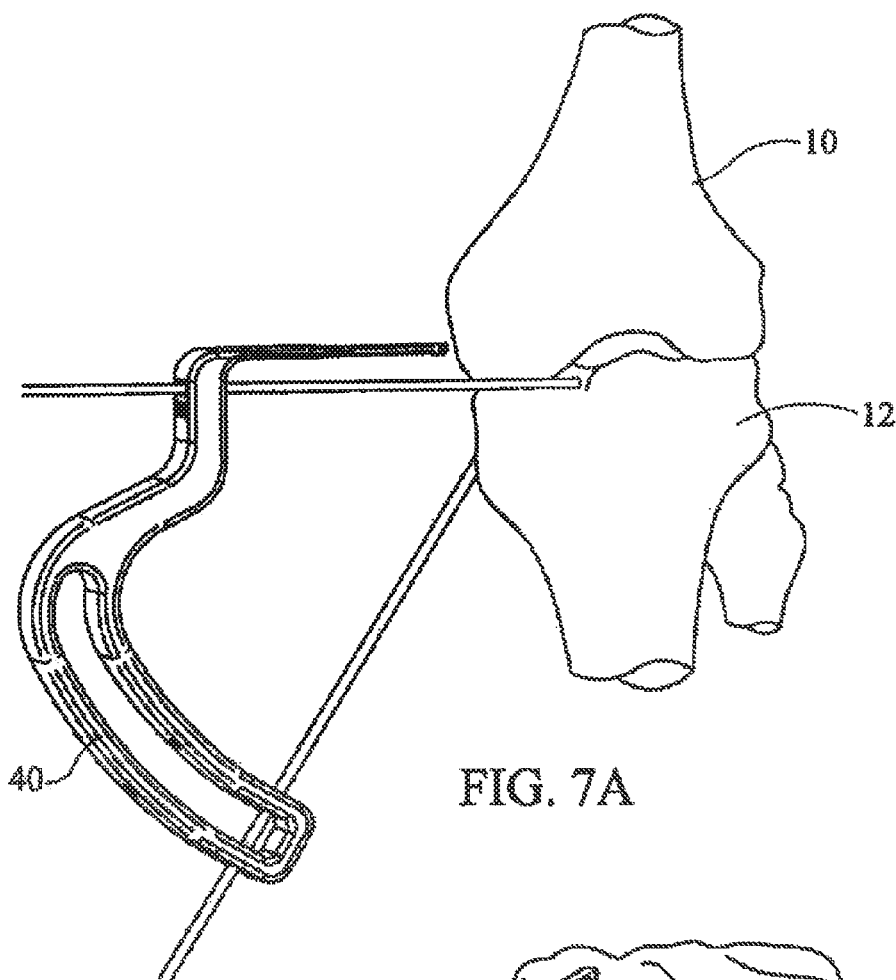
FIG. 7A shows one embodiment of a guide/insertion instrument and a side view of how the guide/insertion instrument may be placed relative to a knee.
Figure 7B:
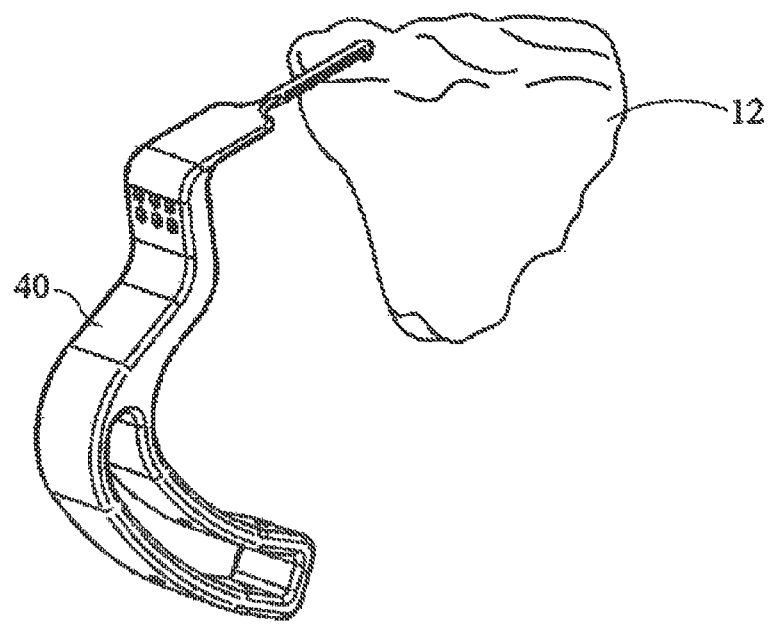
FIG. 7B shows another embodiment of a guide/insertion instrument and a perspective view of how it may be placed relative to a knee.

FIG. 7A shows another embodiment of a guide/insertion instrument 40 and side view of how it may be placed relative to a knee during surgery. FIG. 7B shows the guide/insertion instrument 40 and a perspective view of how it may be placed relative to a knee.

FIGS. 8, 9A-9J, 10A-10B, 11A-11C illustrate a method of treating a knee with OA based on embodiments of the present disclosure. As noted clinical evaluation of the knee of a patient suffering from arthritic pain is performed. Osteoarthritis conditions, generally falling within Grade III or IV, would indicate that additional subchondral damage is present and/or will be evident in the near future. Accordingly, the subchondral bone 14 below the cartilage loss or damage 16 is targeted. The size, volume and orientation of the localized region 92 can be determined from the evaluation or from imaging such as with MRI, as previously described, and based on the findings, the recommended volume of bone void filler is determined from the volume assessment tool. The template 50, shown in FIGS. 3A and 3B, is a transparency with a plurality of curved lines between two intersecting straight lines. In use, the template 50 can be placed over an MRI image to determine the placement of the guide/insertion instrument 40, the appropriate location for the fixed bone portal 62, and the resulting depth to the targeted localized region 92 of the subchondral bone 14.

Figure 8:
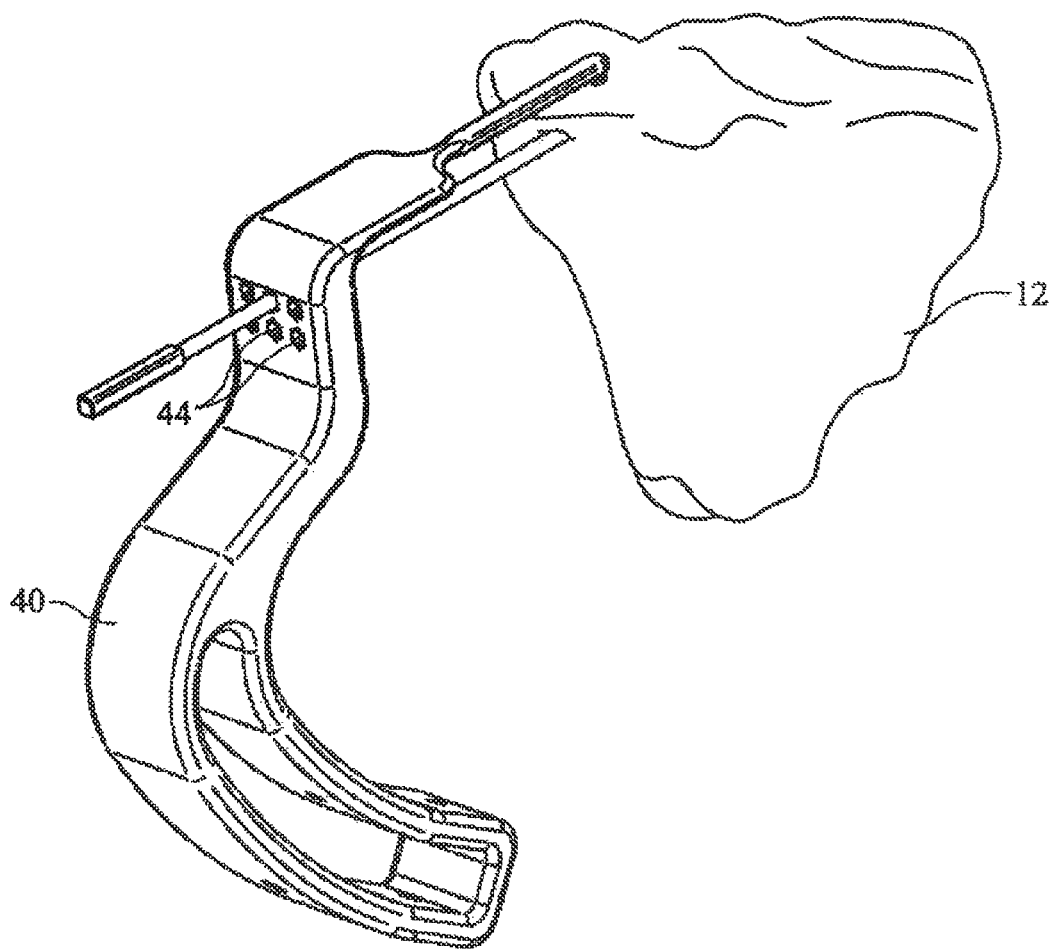
FIGS. 8, 9A-9J, 10A-10B, and 11A-11C illustrate a method of treating a knee based on embodiments of the present disclosure.

Referring now to FIG. 8, the guide/insertion instrument 40 may be positioned such that the location T of the cartilage guide 42 is in on or adjacent to the localized region 92 of interest. In use, the guide/insertion instrument 40 is placed proximate to the joint. The probe may be visually placed on the articular cartilage at the location of the articular cartilage damage 16, for example, using arthroscopy.

The guide/insertion instrument 40 helps determine the access point and angle for the K-wire (included in the instrument system 20), which may be used by the surgeon. For example, in some embodiments for treating a patient's knee, the guide/insertion instrument 40 is configured to treat subchondral bone that is within 5 mm below the tibial surface. In some embodiments, the guide/insertion instrument 40 has a planar, rasped tip for contacting and gripping the articular surface of the knee joint without damaging the cartilage.

Using parallel drill/implant guide 44, a surgeon may then drill parallel, for example, to the articular surface of a patient's knee. In some embodiments, the surgeon drills through or adjacent to the targeted localized region 92 of the subchondral bone 14.

Figure 9A:
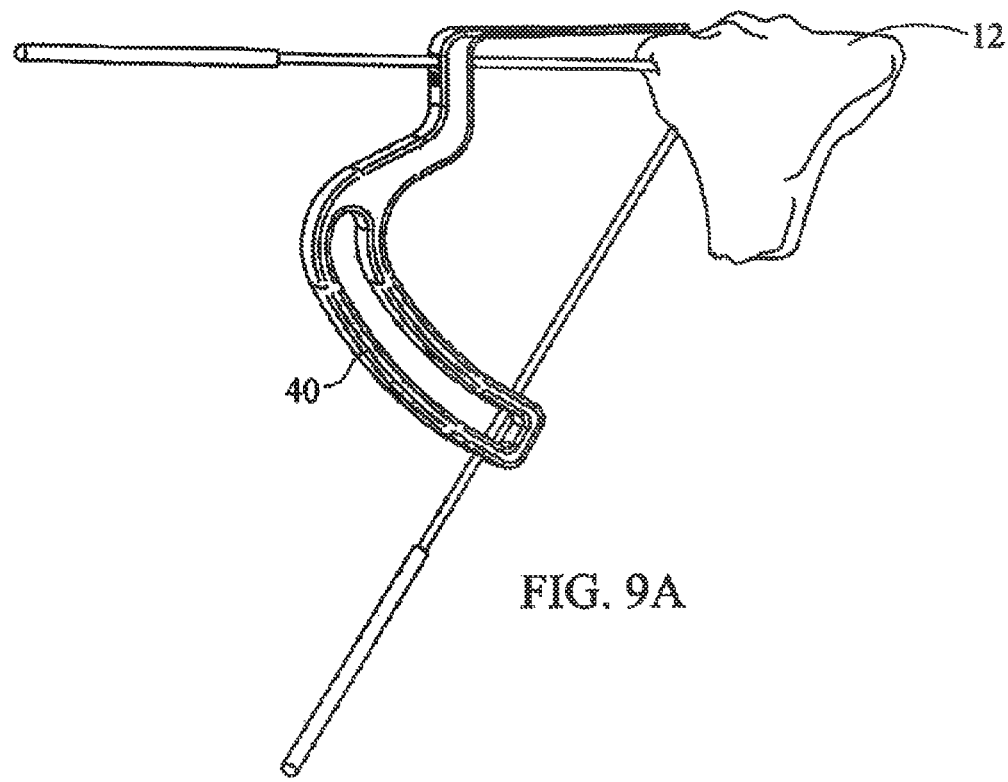

Referring now to FIG. 9A, the surgeon may then drill at an angle to location T of the targeted localized region 92 via angular drill guide/portal 46. The surgeon may select the angle of approach based on a variety of factors, such as the location of the targeted localized region 92, size of the targeted localized region 92, access to the knee, etc. While the guide/insertion instrument 40 is held in place, a K-wire is inserted through the lumen in the adjustable arm and info interior of the bone. Fluoroscopy may be used to verify the position and depth of the wire with respect to the targeted localized region 92. The guide/insertion instrument 40 may then be removed, but the K-wire retains the angle and depth to the targeted localized region 92.

Figure 9B:
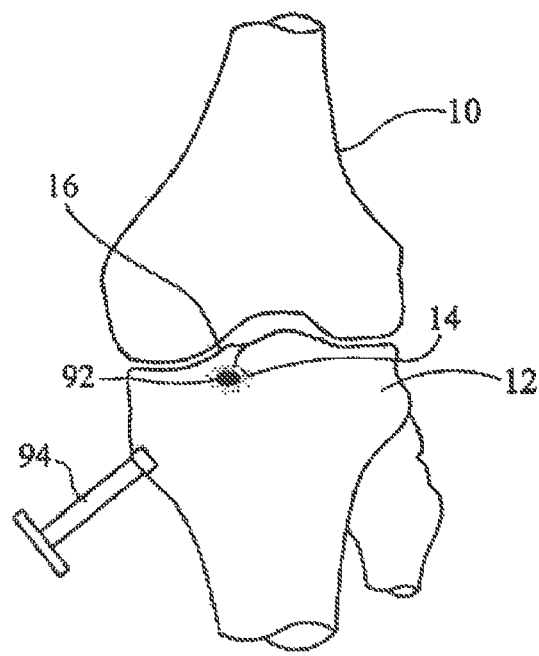
Figure 9C:
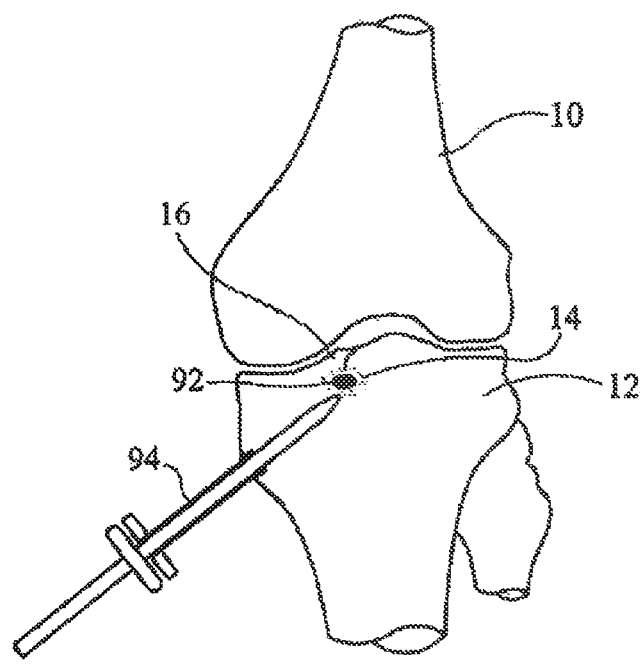
Figure 9D:
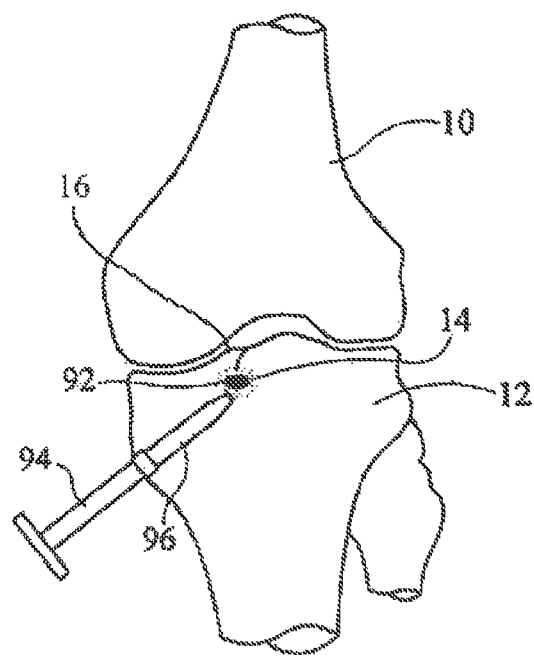

FIGS. 9B-9D illustrate in further detail how a surgeon may drill at an angle to the targeted localized region 92. As shown, the surgeon may install a bone portal 94, for example, using the guide/insertion instrument 40 (not shown).

In use, the guide/insertion instrument 40 is placed proximate to the joint. Based on the information determined from the template 50, the probe tip of guide/insertion instrument 40 is placed on a target location on the articular surface of the knee joint, i.e., in or adjacent to the targeted localized region 92.

The guide/insertion instrument 40 is used to aim a bone portal angle and to set the bone portal depth stop based on the information determined from the template. The guide/insertion instrument 40 may then be removed and the bone portal retains the angle to the targeted localized region 92. During surgery, the bone portal may also bold or steady the guide/insertion instrument 40.

The bone portal 62 (included in the instrument system 20) provides an entry point in the bone for an instrument to gain access to the interior of the bone and to the targeted localized region 92 of the subchondral bone 14. The bone portal 62 may be a single component design having an elongate body. The distal end of the body may include external threads for anchoring the portal 62 to the cortex of the bone. In some embodiments, the portal 62 has an outer diameter of approximately 8 mm. The size of a particular bone portal 62 is selected to support the cortex and prevent possible damage and weakening of the surrounding cortex. The body of the bone portal 62 has a lumen for receiving an instrument therein and a length that allows for an accurate trajectory to the subchondral bone 14. The proximal end of the body has a depth stop for limiting the extent an Instrument received within the lumen may be inserted into the interior of the bone. To facilitate the ease of implementing the PSCP treatment, the bone portal 62 may serve as a working channel, enabling a multitude of instruments to pass through the same access point.

In use, the bone portal 62 can be threadedly anchored to the bone cortex at a location determined from the MRI template. As shown, the bone portal 62 is installed at an angle perpendicular to the bone cortex, resulting in better coupling. Alternatively, the surgeon may use an adjustable bone portal 62 that allows for repeated entry into the bone for multiple locations to be treated with a single bone portal insertion. The portal 62 may be made of a resorbable material, in which case it could provide as an implant left in the cortex after the PSCP procedure is completed. Furthermore, the bone portal 62 may be radiolucent and have at least one marker for identification under imaging.

The surgeon may then drill through the guide/insertion instrument 40 via angular drill guide/portal 46 (not shown) to create a bone cavity 96 to the targeted subchondral space (as shown in FIG. 9D). The drill may be a cannulated drill 70, for example that is used over the K-wire to enlarge the channel to the targeted localized region 92. Other bore creation devices known in the art may be used, including biopsy needles, punches, burrs, reamers, rongeurs and tamps, as well as other types of drills.

Figure 9E:
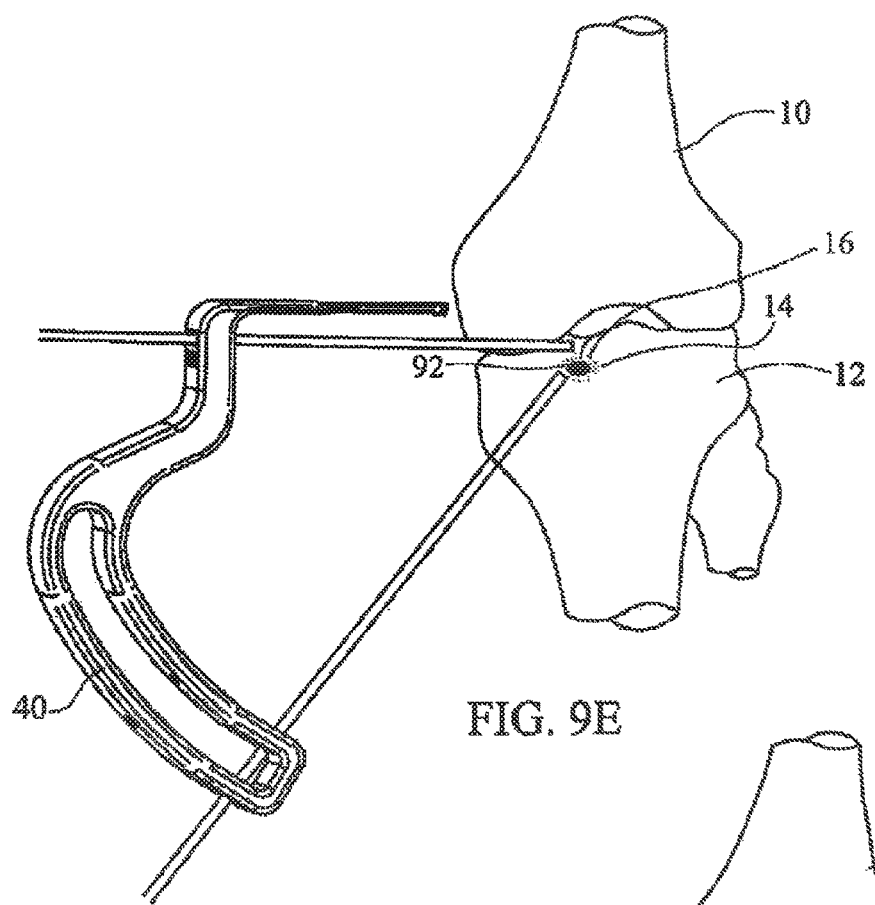

FIG. 9E illustrates how the surgeon may then employ a Kirschner wire or K-wire at the localized region 92 of the subchondral bone 14 below the articular cartilage damage 16. Alternatively, FIG. 9F shows the use of an adjustable bone portal 98 that allows the surgeon to select one or more angles provided by angular drill guide/portal 46 or, for example, to treat multiple localized regions 92 of the subchondral bone 14.

Figure 9F:
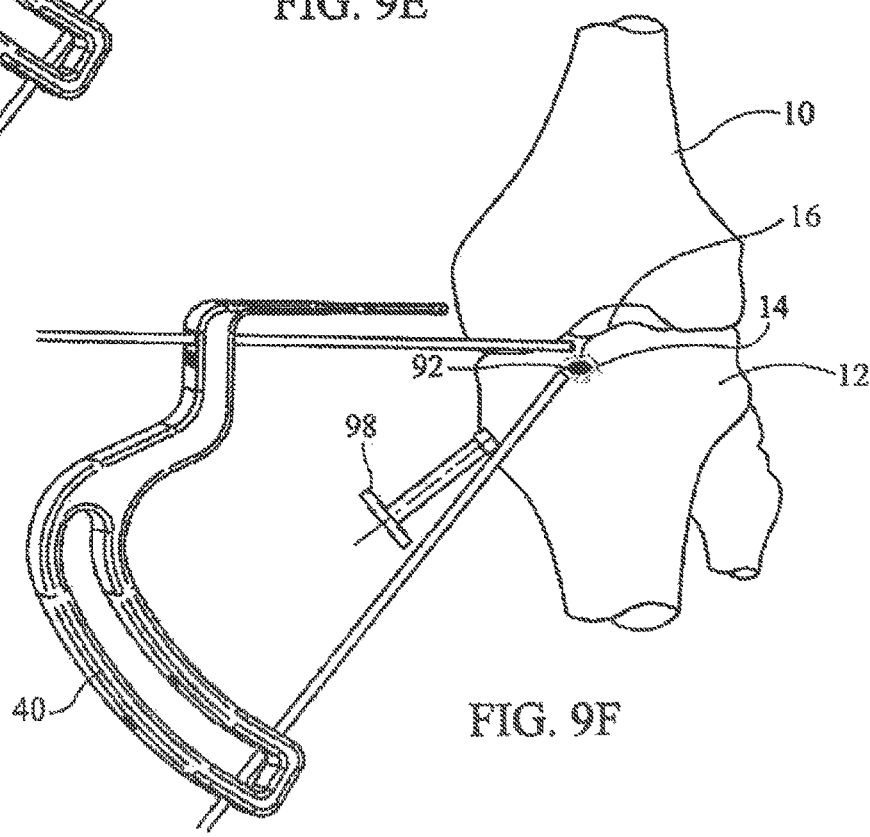
Figure 9G:
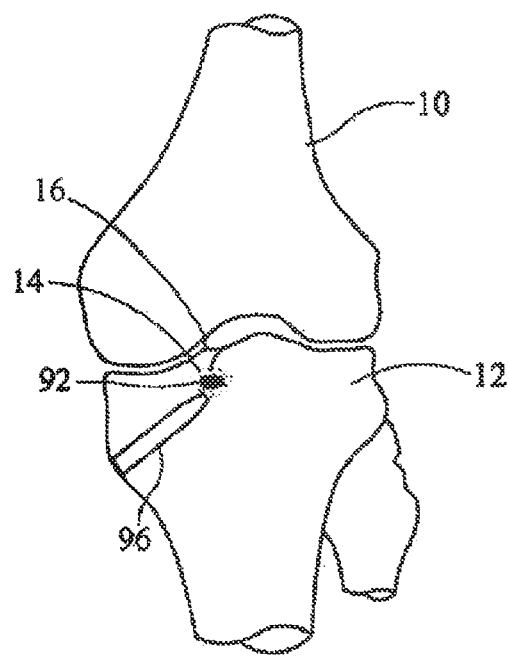
Figure 9H:
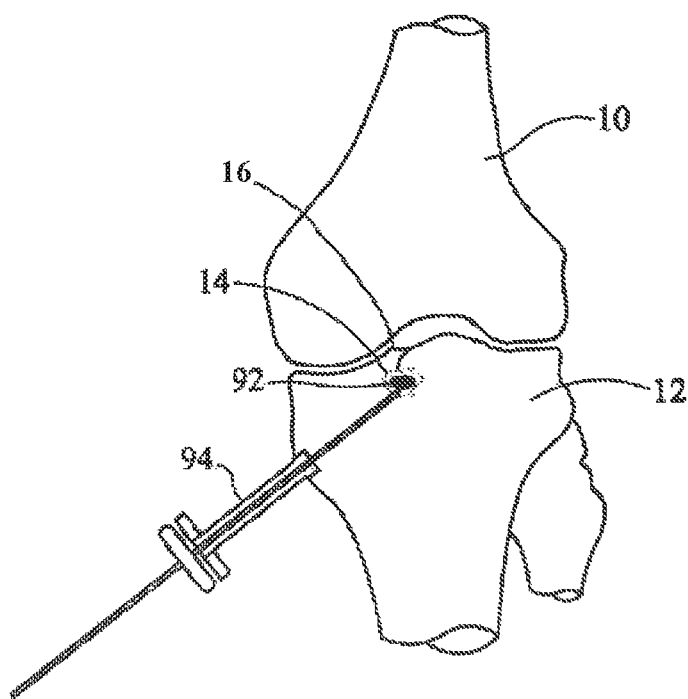
Figure 9I:
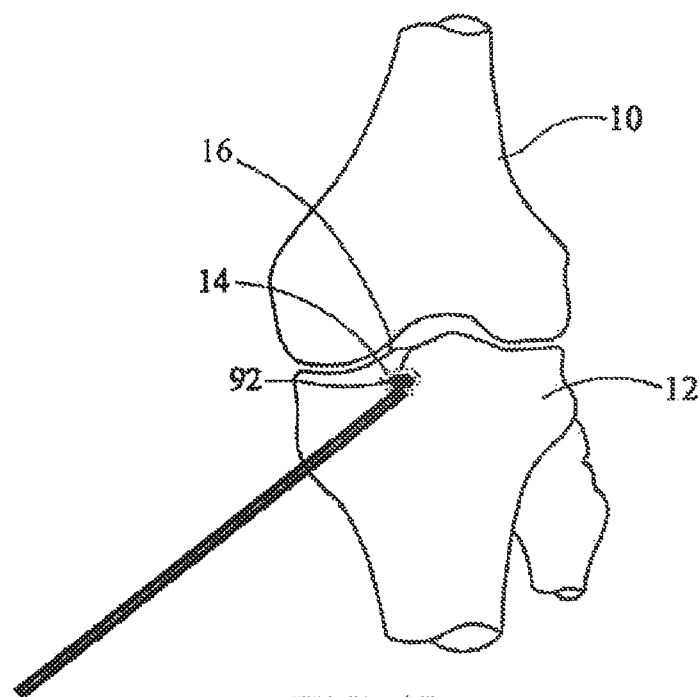
Figure 9J:
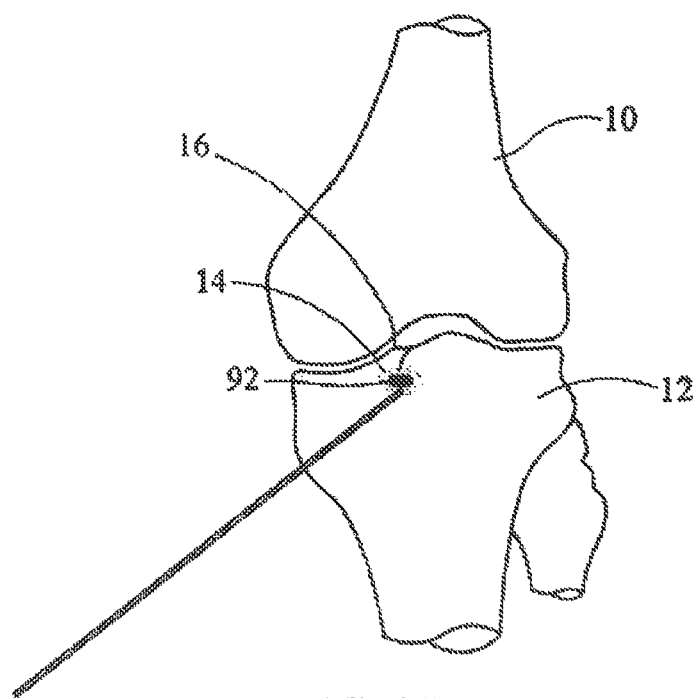

The adjustable bone portal shown in FIG. 9F may be included in the instrument system 20 to provide an entry point in the bone for different instruments to gain access to the inferior of the bone and to a targeted localized region 92, as previously mentioned. In general, the adjustable bone portal has a body component and base component. The base component includes external threads for anchoring the portal to the cortex of the bone and a central opening tor receiving the body component. The outer diameter of the base component is approximately 8 mm, selected to support the cortex and prevent possible damage and weakening of the surrounding cortex with a portal with a larger diameter. The body component may have a lumen for receiving different instruments, and a length that allows for an accurate trajectory to the targeted localized region 92. A proximal end of the body component has a depth stop for limiting the extent an instrument received within the lumen may be inserted into the inferior of the bone. The depth stop may be adjusted according to the depth of the targeted subchondral space within the bone, as measured from the entry point.

In some embodiments, adjustability of the bone portal is achieved through a ball-and-socket arrangement between a socketed central opening in the base component and a ball shaped distal end of the body component. A lock mechanism can be provided to maintain the base and body components in a desired position relative to each other. In another embodiment, adjustability of the bone portal is achieved through a conically shaped central opening in the base component. A locking mechanism can be provided to maintain the base and body components in a desired position relative to each other.

FIGS. 9G-9J illustrates the various ways that a surgeon may treat a knee via bone cavity 96. A cavity creation device is used after a bore creating device is removed to leave an enlarged channel to the targeted localized region 92, and prior to the bone void filler being prepared. As shown, the surgeon may use a K-wire with a depth stop (included in the instrument system 20) to create an access channel to the targeted localized region 92. As shown in FIG. 9G-9J, the K-wire is inserted through the lumen of the bone portal body to the desired depth, which will be reached when the K-wire depth stop contacts the bone portal body depth stop. The K-wire is prevented from being advanced through the articular surface. Fluoroscopy may be used to verify the K-wire position and depth with respect to the targeted localized region 92. If placement is incorrect, the K-wire can be retracted and the bone portal readjusted. The K-wire 64 is then removed.

The surgeon may use a bore creation device (also included in the instrument system 20) to enlarge the access channel created by the K-wire 64 to the fracture. The bore creation device can be an 8-gauge biopsy needle, a core punch, or a fenestrated drill. Each can be provided with a depth stop to prevent penetration through the articular surface of the bone. Other bore creation devices known in the art may be used, including burrs, reamers, rongeurs and tamps, as well as other types of biopsy needles, punches and drills. A cavity creation device in the form of a burr, for example, is inserted through the lumen in the bone portal to the desired depth and is manually moved or activated to create a cavity. Depending on the device used, this may be accomplished by cutting bone, compressing bone, or a combination. If desired, bone tissue surrounding the targeted localized region 92 can also be compacted.

As shown, the surgeon may use a cannulated drill, for example, being inserted through the lumen of the bone portal body until the drill depth stop contacts the bone portal body depth stop. The drill is prevented from being advanced through the articular surface. The drill is then removed, leaving an enlarged channel 96 to the targeted localized region 92.

In another embodiment, a series of cannulas or bone dilators of progressively increasing diameter may be provided. The cannulas or dilators may be used to progressively bore concentric openings within the subchondral bone 14.

Figure 10A:
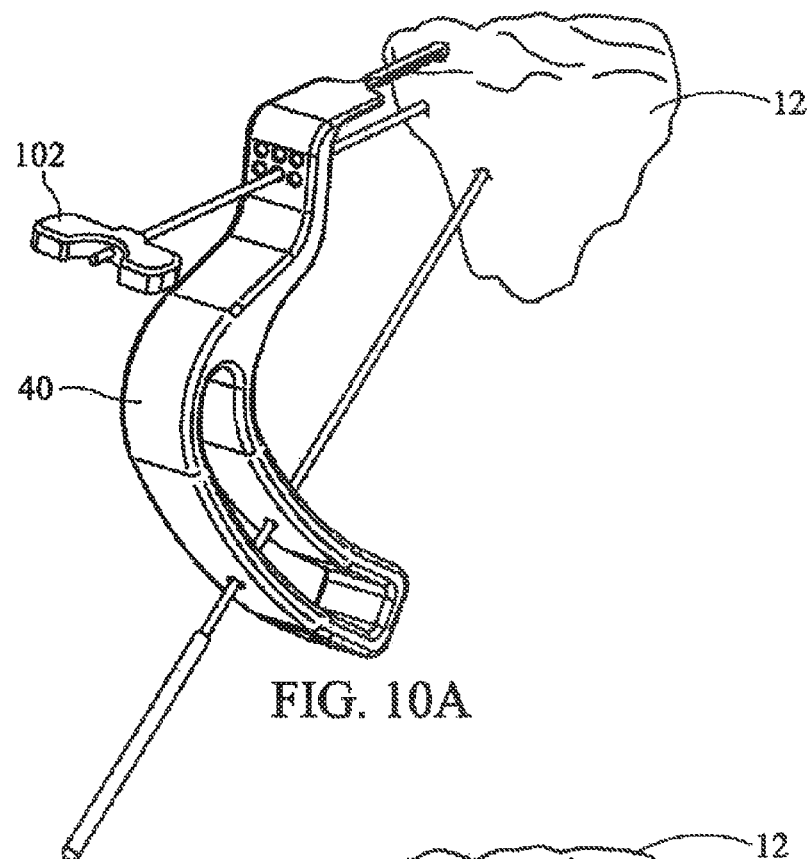

FIG. 10A illustrates another step that a surgeon may perform to treat a patient's knee. In particular, the surgeon may inject a bone hardening material, such as a bone void filler like calcium phosphate (CaP) or a bone cement like a low viscosity polymethylmethacrylate ("PMMA"). During surgery, an injection catheter 66 is filled with a volume of the bone void filler, which is determined from the volume assessment tool (included in the instrument system 20). FIG. 10A shows the injection catheter 66 being inserted and seated to the bone portal. Cement in the catheter 66 prevents bone shards and debris from clogging the catheter 66. Under fluoroscopy, the bone cement is injected from the catheter 66 into the targeted localized region 92 using a syringe 68 with volume and rate controls. The syringe 68 provides tactile feedback as the bone cement is dispensed to fill the targeted localized region 92 and then interdigitate with the immediately surrounding cancellous bone. The catheter 66, syringe 68 and bone portal 62 may then be removed.

In order to prevent bone void filler from leaking out of the hole that remains in the cortex after removal of the bone portal, a portal hole plug (provided in the instrument system 20) may be used. Alternatively, the bone that was removed using the bore creation device during the channel enlargement step may be sized and shaped as a plug to fill the portal hole. Of note, the injection of a bone void filler can occur before or after the implantation of a reinforcing member. If desired, the bone marrow lesion or edema may be aspirated prior to insertion of the implant or infusion of the bone void filler. This aspiration step may be performed through the angular drill guide/portal 46, and suction may be performed through the parallel drill/implant guide 44.

Figure 10B:
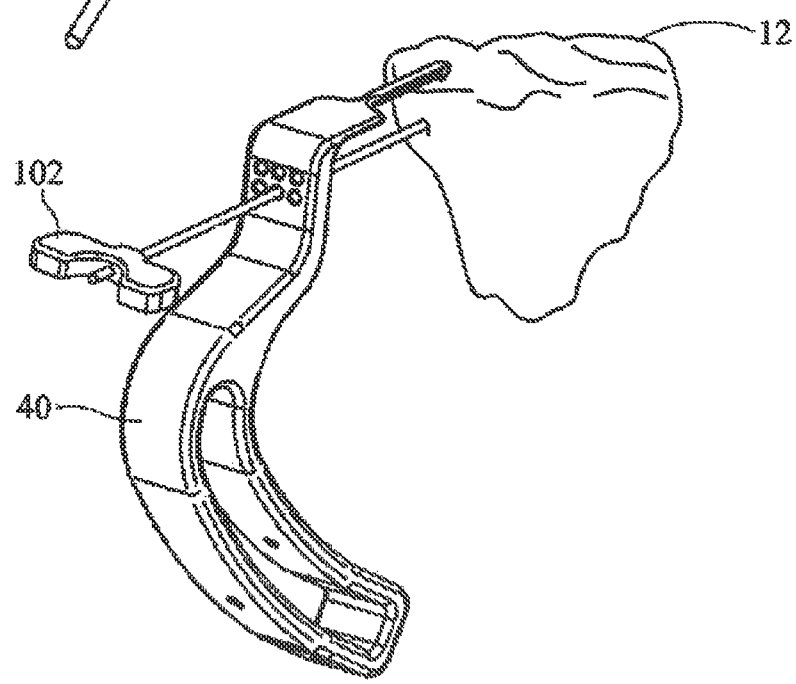

For example, as shown, an 8-gauge needle 102 may be guided via parallel drill/implant guide 44 in or adjacent to the targeted subchondral space. FIG. 10B illustrates another view of the surgeon injecting CaP cement via the parallel drill/implant guide 44. In some embodiments, the surgeon may drill one or more holes at various locations. In addition, the surgeon may leave the drill bits in place in order to stability the tool guide 40.

Alternatively, the surgeon may insert one or more bone conductive pins through the tool guide 40 and into pre-drilled holes. After the implants have been implanted, the tool guide 40 may be removed and pins cut flush to the bone surface.

Figure 11A:
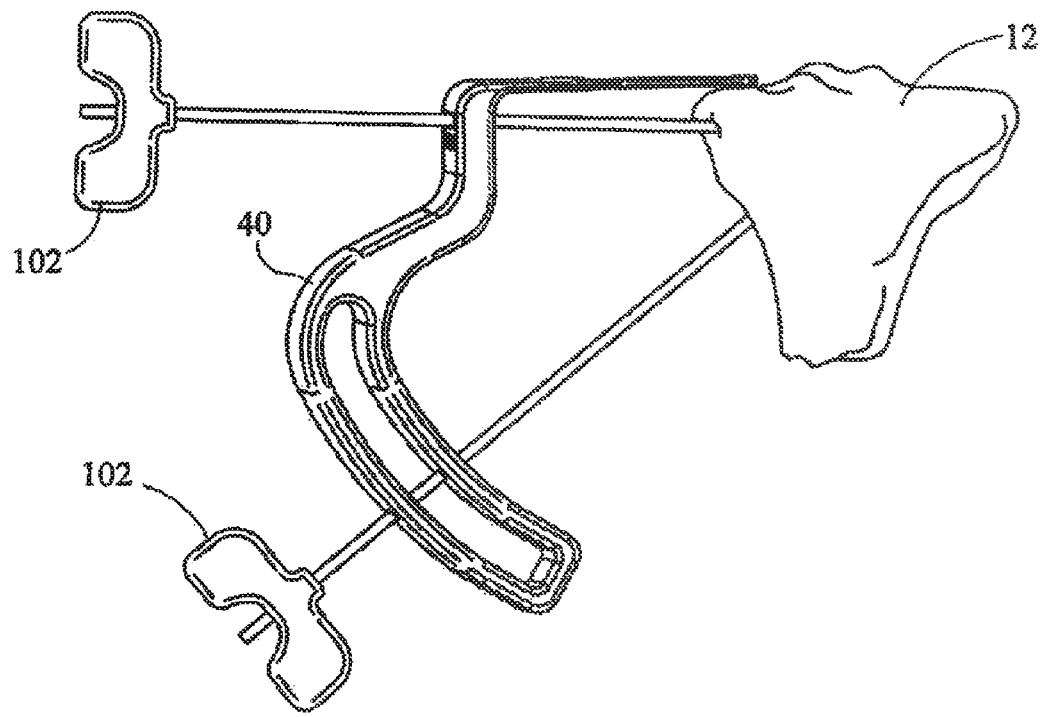
Figure 11B:
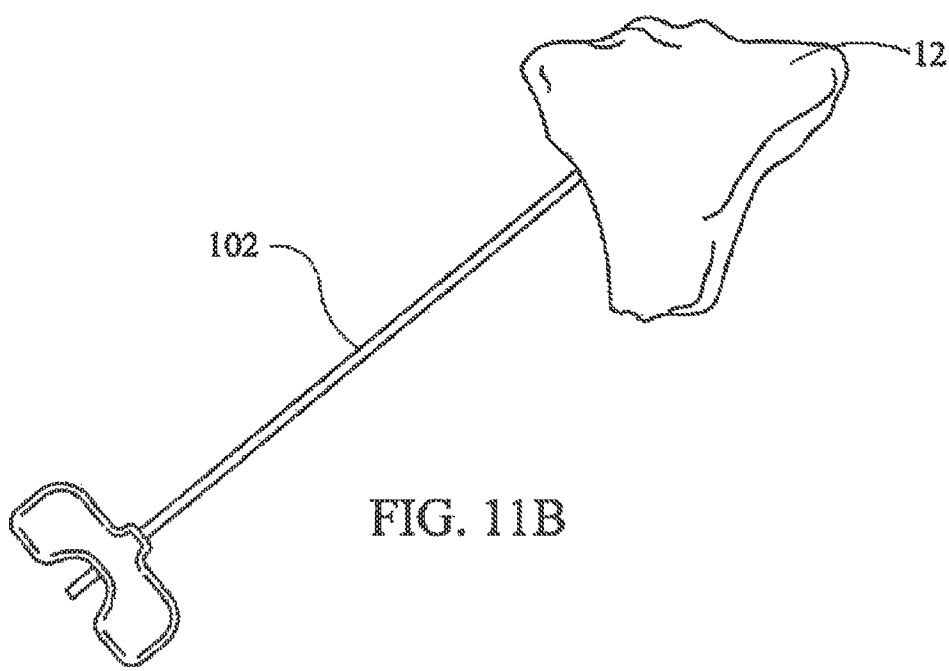
Figure 11C:
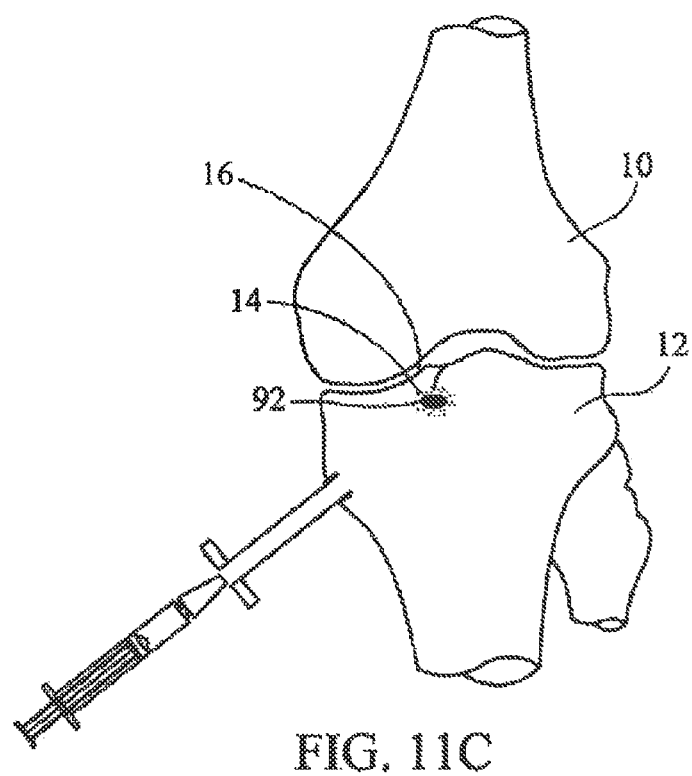

FIGS. 11A-11C illustrate another procedure that a surgeon may perform to treat a patient's knee. For example, FIG. 11A shows the injection of a bone hardening material such as a CaP cement in or adjacent to a bone marrow lesion using 8-gauge needles 102. As shown, the 8-gauge needles 102 are guided using guide/insertion instrument 40 to converge in or adjacent to the targeted localized region 92. Alternatively, as shown in FIG. 11B, once the drills have been inserted, the surgeon may remove the guide/insertion instrument 40 (not shown) and guide an 8-gauge needle 102 over the drill to inject the CaP cement in or adjacent to the targeted localized region 92. For example, a catheter 66 filled with bone cement is then injected into the bone cavity 96 to fill the cavity and then any interstitial space of surrounding uncompressed cancellous bone.

Figure 13:
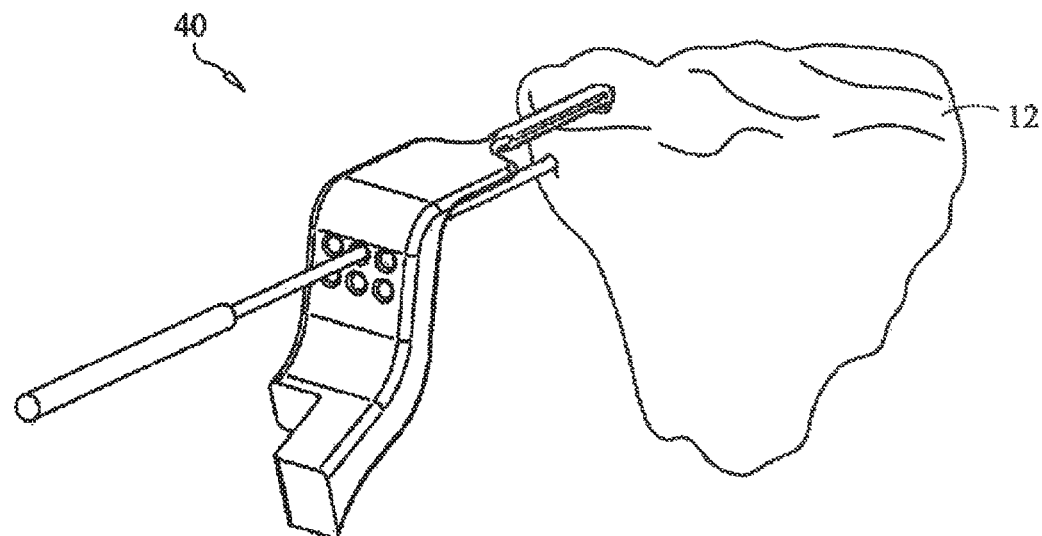

FIGS. 12-16 illustrate a method of treating subchondral bone based on another embodiment of the present invention, in particular, as shown in FIG. 12, the guide/insertion instrument 40 may comprise a detachable handle that the surgeon removes Initially to position the guide/insertion instrument 40, for example, on the articular surface. Referring now to FIG. 13, the surgeon may then drill via parallel drill/implant guide 44 towards the targeted localized region 92 of the subchondral bone 14.

Figure 14:
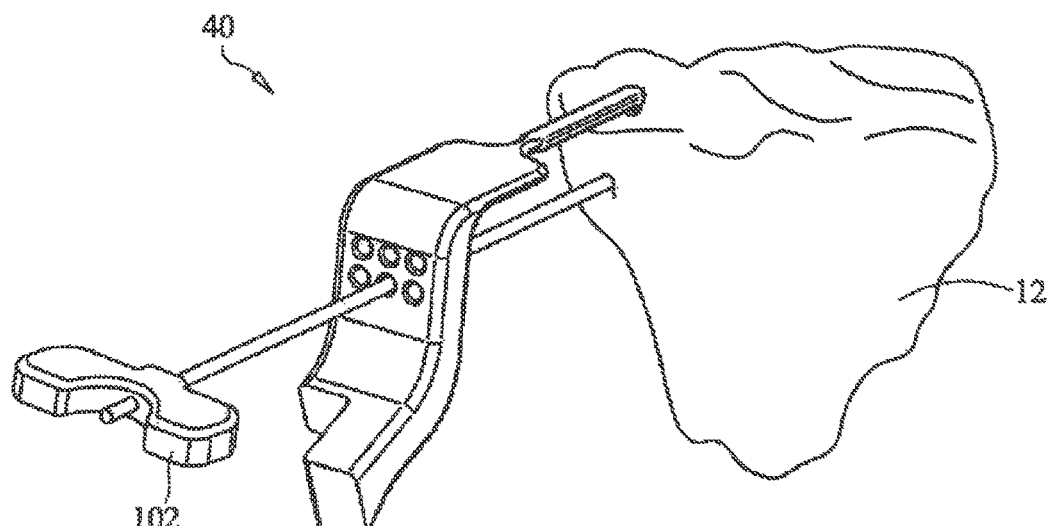
Figure 15:
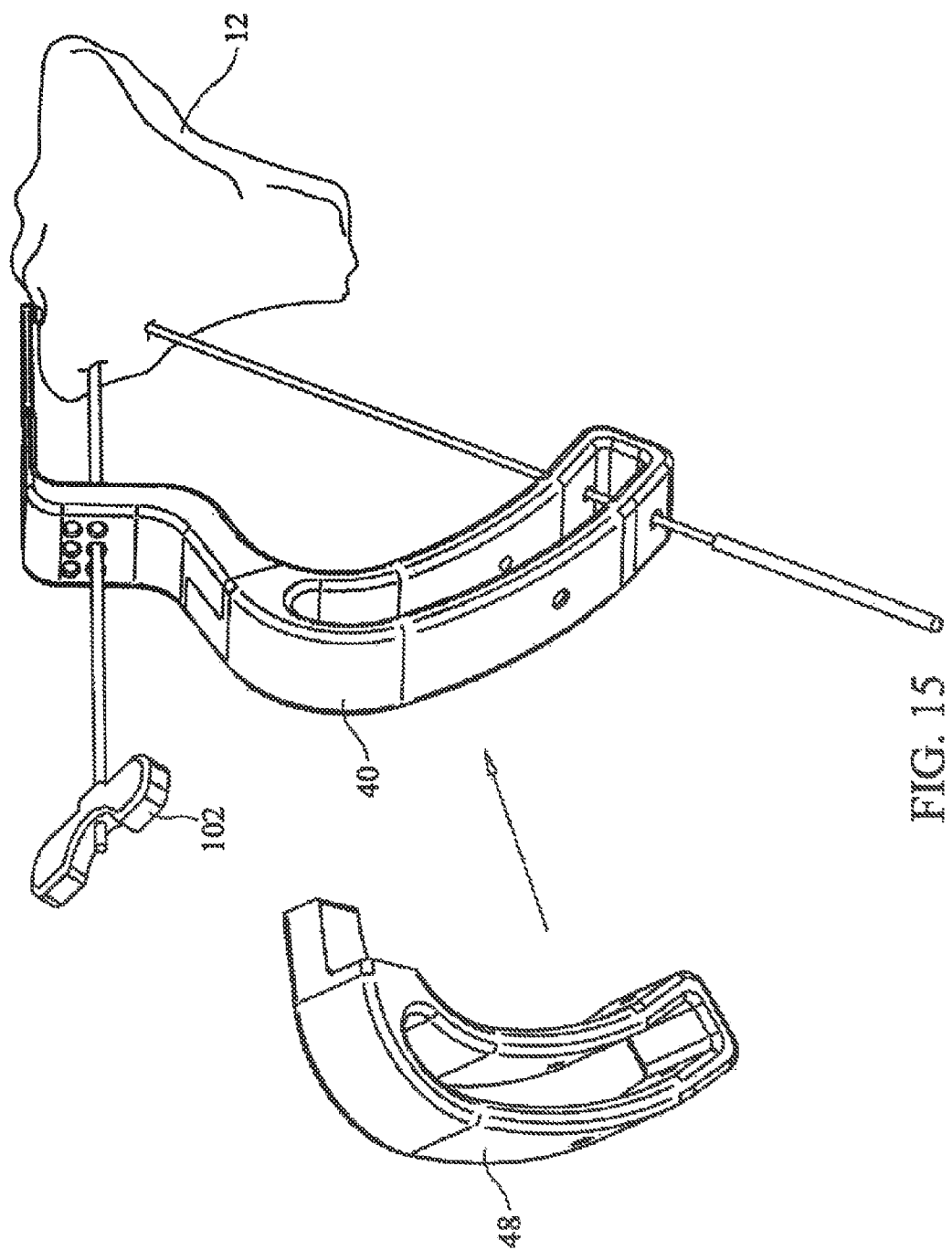
Figure 16:
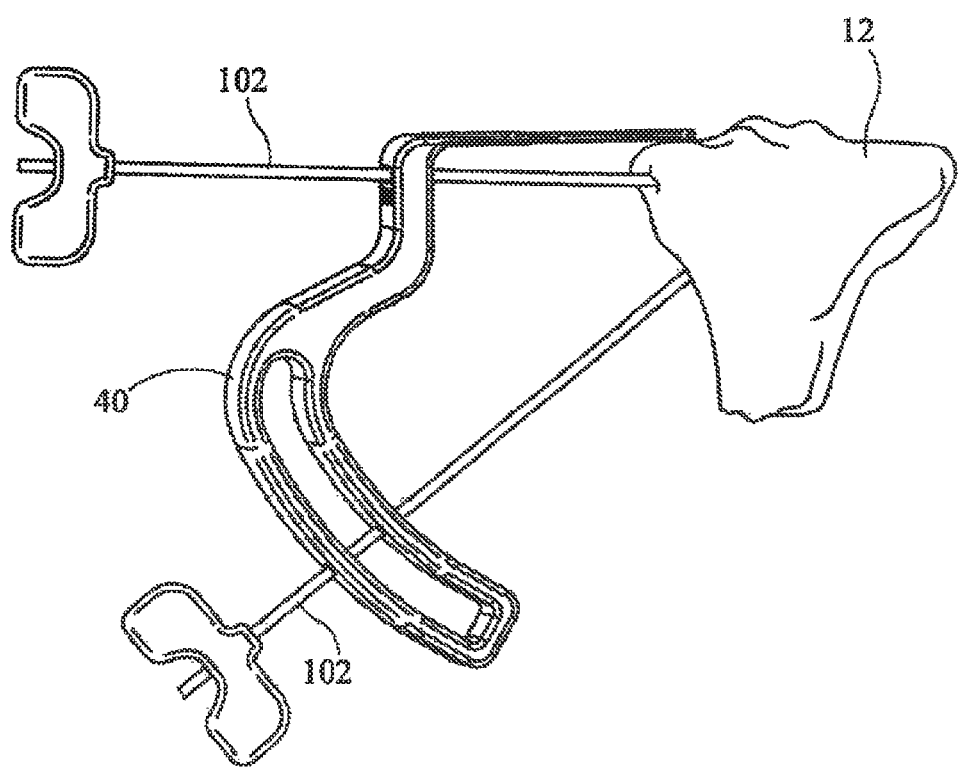

As shown in FIG. 14, the surgeon injects CaP cement using an 8-gauge needle over the drill in or adjacent to the targeted localized region 92. Next, as shown in FIG. 15, the surgeon may reattach the detachable handle 48 to the guide/insertion instrument 40 and drill in or through the targeted localized region 92 via angular drill guide/portal 46. As shown in FIG. 16, if desired, the surgeon may then inject CaP cement using a cannula with injection port or fenestrated distal tip for target placement or dispersion of the bone void filler, or the 8-gauge needle 102, over the drill to inject CaP cement in or adjacent to the bone marrow lesion via angular drill guide/portal 46.

As already mentioned, in one treatment modality a reinforcing member comprising an implantable device can be inserted into the localized region 92 of the subchondral bone 14 below the area of articular cartilage damage 16. The implantable device could be implanted subchondrally to mechanically support the subchondral bone below the cartilage loss, thereby prevent the manifestation of BML or BME in the bone. Those skilled in the art will recognize multiple reinforcing members can be implanted in and/or adjacent to the targeted localized region 92.

In general, the implantable device serves to adequately distribute stresses placed on the bone. The implantable device may be bioactive and configured to have an appropriate rigidity/flexibility and other characteristics, such as porous or non-porous coatings, as desired. In particular, the implantable device may be sufficiently strong or stiff to make it capable of being implanted in bone and avoid stress concentration, for example, in the subchondral region of the bone. Accordingly, the implantable device may have various dimensions and stiffness.

In some embodiments, the implantable device is implanted free of bonds to the bone. Thus, the implantable device is not, for example, glued, cemented, stapled, stitched, clamped or screwed to the bone. However the implantable device may naturally or be configured to eventually bond to the bone via biological processes in situ.

In certain embodiments, a syringe (optionally with a needle) can be used to inject a fluid into a bone so as to form a reinforcing member or implantable device in situ and/or stimulating bone repair. This step can be conducted with or without first creating an opening in the bone. The fluid is preferably a liquid, semi-solid, gel, hydrogel, dispersion or slurry. After injection, the fluid can remain fluid-like, or may cure to a more solid-like state. For example, the injected fluid can cross-link or polymerize from a liquid to form a semi-solid, gel or solid. Fluids that cure in situ can be self-curing or can cure in response to curing means, such as, e.g., radiation (e.g., UV light), heat (e.g., body temperature), moisture and/or a curing agent.

In other embodiments, the reinforcing member is solid in nature and may be rigid or malleable. In these embodiments, the surgeon creates a small opening in the vicinity of the targeted localized region 92. Suitable surgical tools for this task include standard bone instruments (e.g., chisels, drills, etc.) and instruments, such as a guide/insertion instrument, designed for use in the method of the invention.

A surgeon can implant the reinforcing member by studying a previously captured image of the bone and manually estimating the location and boundaries of the targeted localized region 92 of the subchondral bone 14. Alternatively, a surgeon can be provided with additional guidance during surgery. For example, surgery can be conducted using real-time imaging, robotic devices, one or more braces that maintain the joint in a position consistent with captured images of the joint and/or labels, etc. Suitable labels include but are not limited to radioactive labels, such as Technetium-99 and other objects, such as fiducial markers.

As noted, the methods described herein may provide various treatment modalities and employ different types of reinforcing members. The reinforcing member may have various forms and shapes to maximize its surface area and reduce stress of the bone when implanted. For example, the reinforcing member may be in the form of a rod having a triangular profile, a rectangular profile, or a circular profile. The reinforcing member may be planar, e.g., relatively long in two dimensions and relatively short in a third dimension. Planar reinforcing members in accordance with the invention can have a thickness which is ≤50% of the length and ≤50% of the width of a rectangular reinforcing member (or ≤50% of the diameter in the case of a circular reinforcing member or ≤50% of the height and ≤50% of the base in the case of a triangular reinforcing member).

In other embodiments, the reinforcing member may have a wedge-shaped edge on at least one edge or a wedge or ramp shape when viewed from the side. A wedge-shaped edge may be adapted to facilitate inserting the reinforcing member into the bone. Thus, the particular angle and other dimensions of the wedge may be dictated by factors that are known in the art. As a wedge-shaped implant, the reinforcing member may be similar to standard surgical tools, such as osteotomes, or comprise blade plates or osteotomy staples. Further, the reinforcing member may be an expandable device that can span the targeted localized region 92. In one embodiment the reinforcing member may be an expandable screw, such as an osseoscrew.

In other embodiments, the reinforcing member may be in the form of a closed disc, an open disc, a screw-shaped device, or an elongated pin. In addition, the reinforcing member may have a square profile, rectangular profile with rounded edges, or an I-beam profile. Alternatively, the reinforcing member can be an injection cement diffuser. In some embodiments, the reinforcing member may be approximately 3 mm thick.

In some embodiments, the reinforcing member may be customized to the patient. For example, using 3-dimensional imaging technology. It may be desirable to provide an implant that matches precisely the anatomical localized region 92 of the subchondral bone 14 where the reinforcing member is to be placed. This would ensure conformability and avoid a less than perfect match between the implant and the targeted localized region 92 of the subchondral bone 14.

The reinforcing member may be porous and/or fenestrated to allow for bone ingrowth. Reinforcing member comprises a physiologically compatible material that has sufficient durability to reinforce the overstressed bone of the bone lesion and bear physiologic loads. Materials for the reinforcing member can include metals, such as titanium, stainless steel, alloys of cobalt and chrome, tantalum, alloys of titanium and nickel and other superelastic metal alloys. Porous, titanium, titanium "foam", tantalum, trabecular metals, nanoceramics, porous nitinol, or other highly porous nanomaterials, and chrome cobalt may also be employed in the reinforcing member.

The reinforcing member may comprise a functional coating, such as, hydroxyapatite plasma coating, titanium nitrate or bioactive glass. In addition, the reinforcing member may undergo some form of surface treatment including acid etching, grit blast, or plasma spray. The reinforcing member may also comprise structural enhancements such as meshes, and include autograft. The member 16 may also be formed of, or include, porous metals like tantalum or ACTIPORE.

Other embodiments comprise the use of bone, such as autografts, allografts, and artificial or synthetic bone substitutes. Certain embodiments comprise the use of polymeric materials. A combination of materials, such as a porous metal applied to a carbon fiber implant may be employed in the reinforcing member.

The reinforcing member can be osteogenic, osteoinductive, and/or osteoinductive. Osteoinductive materials that may be used include but are not limited to collagen and the various forms of calcium phosphates including hydroxyapatite, tricalcium phosphate, and fluoroapatite. Suitable osteoinductive substances include but are not limited to bone morphogenetic proteins (e.g., rhBMP-2), demineralized bone matrix, transforming growth factors (e.g., TGF-beta), osteoblast cells, and various other organic species known to induce bone formation. Bone marrow, blood plasma, or morselized bone of the patient, or commercially available materials may also be used.

The reinforcing member may be treated prior to implantation. For example, the reinforcing member may be dipped or coated with bone conductive or bone inductive material. Osteoinductive materials, such as BMP, may be applied to, for example, by immersing the reinforcing member in an aqueous solution of this material in a dilute suspension of type I collagen. Osteoinductive materials such as TGF-beta may be applied from a saline solution containing an effective concentration of TGF-beta, or may be carried in the resilient material. Of course, other biologics may be applied by any method known in the art.

The reinforcing member can be resorbable or non-resorbable. For example, the reinforcing member may comprise PEEK, PGA, or PLA material. Electrical stimulation can also be applied to the bone to promote bone healing. The reinforcing member may also be capable of imbibing bone stimulating material, such as porous nitinol, e.g., ACTIPORE™ or other form of porous coated titanium or periapatite coated titanium.

In some embodiments, implantation of the reinforcing member may be achieved step-wise in multiple stages. For example, the reinforcing member may be constructed to be implanted at an initial stage to establish primary fixation, then at a subsequent stage additional implantation or assembly can be performed to add increased pull-out strength and other reinforcing properties to the fully assembled reinforcing member.

Other forms of implantable devices and variations of the reinforcing member are also disclosed in co-pending and co-owned U.S. patent application Ser. No. 12/950,306, filed Nov. 19, 2010 and entitled "IMPLANTABLE DEVICES FOR SUBCHONDRAL TREATMENT OF JOINT PAIN," U.S. patent application Ser. No. 12/950,273, filed Nov. 19, 2010 and entitled "IMPLANTABLE DEVICES FOR SUBCHONDRAL TREATMENT OF JOINT PAIN," and U.S. patent application Ser. No. 12/950,183, filed Nov. 19, 2010 and entitle "BONE-DERIVED IMPLANTABLE DEVICES FOE SUBCHONDRAL TREATMENT OF JOINT PAIN," the contents of which are herein incorporated in their entirety by reference.

Various criteria may be considered in the selection of any one of the treatment modalities, or combination of modalities, for treating the subchondral bone in accordance with principles of the present disclosure. For example, a reinforcing member as an implantable device may be selected based on the severity, location, and size of the arthritic damage or condition of the bone (i.e., the condition of the cartilage loss or damage). Factors considered may include, among other things, the nature of the damage, extent of the damage, location of the damage, etc. For example, cartilage loss or damage at the edge near the articular surface or periphery of a joint may be often considered eligible for treatment due to edge-loading effects as well as the likelihood of bone hardening at these locations.

In early stages of the disease, patients may have no or minimal OA symptoms. However, if available and applicable, one of the factors in determining which treatment modality to select include the length of time that a patient reports suffering pain. Subjective pain perception, such as VAS scores reported by the patient (if available or applicable), may also be considered in selecting a treatment modality. Other subjective scoring systems may be used in the evaluation phase. For example, the well-known IKDC subjective score, which measures a patient's ability to perform a variety of tasks, may be used as an indication. The lower the IKDC score, the more limited a patient's function.

In addition, the patient's physiology and other characteristics may be considered in determining which of the treatment modalities to perform. For example, the patient's age may be a factor. A patient's other physical characteristics may be considered as well, such as their standing alignment of the patient, i.e., varus and valgus, weight, body mass index, etc.

While the invention is described in the context of osteoarthritis of the knee, it is not limited to such condition. Other conditions that can be treated in accordance with the invention include but are not limited to osteoarthritis of joints other than the knee. For example, the PSCP treatments may be used to treat other joints, such as the shoulder, hip, ankle, and spine. Moreover, in some embodiments, the PSCP treatments may be coupled to other forms of joint pain treatment. For instance, in the knee, the PSCP treatment may be employed in conjunction with an arthroscopy or cartilage resurfacing procedure. In such cases, the PSCP procedure itself becomes a component in a multi-step treatment process to address the overall pain management and treatment of the joint.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A method for treating subchondral bone in a first bone adjacent a knee joint having a meniscus to try to prevent or delay the onset of a bone marrow edema in subchondral bone of the first bone, the first bone having articular cartilage, the subchondral bone occurring under the articular cartilage, the method comprising:
   obtaining imaging of the first bone that is usable to determine if the imaging detects a bone marrow edema in the subchondral bone, wherein the imaging obtained includes one or more types of imaging that each fail to detect a bone marrow edema in the subchondral bone;
   creating, despite the one or more types of imaging failing to detect a bone marrow edema in the subchondral bone, an access path to the subchondral bone, wherein said creating is conducted without creating a void in the subchondral bone that opens into the overlying articular cartilage of the first bone so as to preserve an existing condition of the overlying articular cartilage of the first bone; and
   injecting an injectable fluid material into the subchondral bone via the access path for treating the subchondral bone, wherein the injectable fluid material is left in the subchondral bone without also delivering and leaving a solid structural implant in the subchondral bone in addition to the injectable fluid material, wherein the injectable fluid material includes an osteogenic, osteoconductive and/or osteoinductive material.

2. The method of claim 1, wherein the one or more types of imaging includes an MRI.

3. The method of claim 1, wherein the injectable fluid material includes bone marrow.

4. The method of claim 1 further comprising identifying tears in the meniscus.

5. The method of claim 1 further comprising identifying damage in the articular cartilage of the first bone.

6. The method of claim 5, wherein the damage in the articular cartilage includes articular cartilage edema.

7. The method of claim 5, wherein the damage in the articular cartilage includes tears in the articular cartilage.

8. The method of claim 5, wherein the damage in the articular cartilage exposes subchondral bone.

9. The method of claim 5, wherein said identifying damage in the articular cartilage includes visualizing the damage arthroscopically.

10. The method of claim 1 further comprising arthroscopically visualizing the first bone.

11. The method of claim 1 further comprising arthroscopically repairing a portion of the articular cartilage.

12. The method of claim 1 further comprising arthroscopically repairing a meniscal tear.

13. The method of claim 1, wherein the injectable fluid material is effective to reinforce the subchondral bone.

14. The method of claim 1, wherein the injectable fluid material includes a calcium phosphate.

15. The method of claim 1, wherein the subchondral bone is in a proximal tibia.

16. The method of claim 1, wherein the subchondral bone is in a distal femur.

* * * * *